United States Patent
Gatto et al.

(10) Patent No.: US 7,033,645 B2
(45) Date of Patent: Apr. 25, 2006

(54) PROCESS FOR APPLYING A STABLE SKIN CARE COMPOSITION TO A SUBSTRATE

(75) Inventors: Joseph Anthony Gatto, Loveland, OH (US); Thomas Robert Hanser, Taylor Mill, KY (US); James Anthony Staudigel, Cincinnati, OH (US); Thomas James Klofta, Cincinnati, OH (US); Ronald Dean Cramer, Cincinnati, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 36 days.

(21) Appl. No.: 10/845,926

(22) Filed: May 13, 2004

(65) Prior Publication Data
US 2004/0208984 A1    Oct. 21, 2004

Related U.S. Application Data

(60) Division of application No. 10/417,459, filed on Apr. 16, 2003, now Pat. No. 6,793,930, which is a continuation of application No. 09/563,638, filed on May 2, 2000, now Pat. No. 6,570,054, which is a continuation-in-part of application No. 09/316,691, filed on May 21, 1999, now abandoned.

(51) Int. Cl.
*B05D 1/00* (2006.01)
(52) U.S. Cl. ............ 427/374.1; 427/394; 427/398.1
(58) Field of Classification Search .......... 427/374.1, 427/374.4, 394, 398.1
See application file for complete search history.

(56) References Cited

U.S. PATENT DOCUMENTS

| | | |
|---|---|---|
| 2,804,424 A | 8/1957 | Stirn et al. |
| 3,489,148 A | 1/1970 | Duncan et al. |
| 3,490,454 A | 1/1970 | Goldfarb et al. |
| 3,585,998 A | 6/1971 | Hayford et al. |
| 3,875,942 A | 4/1975 | Roberts et al. |
| 3,896,807 A | 7/1975 | Buchalter |
| 3,902,493 A | 9/1975 | Baier et al. |
| 4,034,077 A | 7/1977 | Hill et al. |
| 4,112,167 A | 9/1978 | Dake et al. |
| 4,263,363 A | 4/1981 | Buck et al. |
| 4,324,247 A | 4/1982 | Aziz |
| 4,513,051 A | 4/1985 | Lavash |
| 4,556,560 A | 12/1985 | Buckingham |
| 4,569,343 A | 2/1986 | Kimura et al. |

(Continued)

FOREIGN PATENT DOCUMENTS

CA    2019557    12/1990

(Continued)

*Primary Examiner*—Erma Cameron
(74) *Attorney, Agent, or Firm*—Eric T. Addington; Dara M. Kendall; KEn K. Patel

(57) ABSTRACT

The present invention relates to an absorbent article having a stable skin care composition disposed on its skin-contacting surface. The skin care composition is readily transferable to the skin via normal contact, wearer motion, and/or body heat. Importantly, the skin care composition contains at least one skin care ingredient imparting visible skin benefits to the skin upon transfer to the skin and at least one rheological agent for stabilizing the composition such that agglomeration, stratification and/or settling of the composition are minimized. The present invention also relates to a process for making the absorbent articles having a stable skin care composition disposed thereon.

10 Claims, 3 Drawing Sheets

U.S. PATENT DOCUMENTS

| | | |
|---|---|---|
| 4,623,339 A | 11/1986 | Ciraldo et al. |
| 4,657,537 A | 4/1987 | Zimmerer |
| 4,666,765 A | 5/1987 | Caldwell et al. |
| 4,685,909 A | 8/1987 | Berg et al. |
| 4,690,821 A | 9/1987 | Smith et al. |
| 4,704,112 A | 11/1987 | Suzuki et al. |
| 4,753,643 A | 6/1988 | Kassai |
| 4,790,836 A | 12/1988 | Brecher |
| 4,842,593 A | 6/1989 | Jordan et al. |
| 4,882,204 A | 11/1989 | Tenenbaum |
| 4,900,317 A | 2/1990 | Buell |
| 4,904,524 A | 2/1990 | Yoh |
| 4,911,932 A | 3/1990 | Clum et al. |
| 4,929,498 A | 5/1990 | Suskind et al. |
| 4,959,059 A | 9/1990 | Eilender et al. |
| 4,990,144 A | 2/1991 | Blott |
| 4,996,238 A | 2/1991 | Matravers |
| 5,034,444 A | 7/1991 | Yun et al. |
| 5,043,155 A | 8/1991 | Puchalski et al. |
| 5,091,193 A | 2/1992 | Enjolras et al. |
| 5,194,261 A | 3/1993 | Pichierri |
| 5,264,460 A | 11/1993 | Jakobson et al. |
| 5,321,098 A | 6/1994 | Lal |
| 5,362,488 A | 11/1994 | Sibley et al. |
| 5,370,132 A | 12/1994 | Weber et al. |
| 5,415,649 A | 5/1995 | Watanabe et al. |
| 5,436,007 A | 7/1995 | Hartung et al. |
| 5,444,096 A | 8/1995 | McCrea et al. |
| 5,509,915 A | 4/1996 | Hanson et al. |
| 5,525,345 A * | 6/1996 | Warner et al. ............. 424/402 |
| 5,525,346 A | 6/1996 | Hartung et al. |
| 5,558,655 A | 9/1996 | Jezzi et al. |
| 5,607,760 A | 3/1997 | Roe |
| 5,609,587 A | 3/1997 | Roe |
| 5,618,522 A | 4/1997 | Kaleta et al. |
| 5,618,529 A | 4/1997 | Pichierri |
| 5,635,191 A | 6/1997 | Roe et al. |
| 5,643,588 A | 7/1997 | Roe et al. |
| 5,833,967 A | 11/1998 | Ramin |
| 5,871,760 A * | 2/1999 | Doughty et al. ............ 424/401 |
| 6,013,271 A * | 1/2000 | Doughty et al. ............ 424/401 |
| 6,149,934 A | 11/2000 | Krzysik et al. |
| 6,153,209 A * | 11/2000 | Vega et al. ................. 424/404 |
| 6,204,208 B1 | 3/2001 | Krzysik et al. |
| 6,217,890 B1 | 4/2001 | Paul et al. |
| 6,287,581 B1 | 9/2001 | Krzysik et al. |
| 6,296,862 B1 | 10/2001 | Paul et al. |
| 6,316,013 B1 | 11/2001 | Paul et al. |
| H2013 H * | 2/2002 | Boyd et al. ................. 424/401 |
| 6,716,204 B1 * | 4/2004 | D'Acchioli et al. ... 604/385.19 |
| 2003/0130635 A1 * | 7/2003 | Tate et al. .................. 604/367 |

FOREIGN PATENT DOCUMENTS

| | | |
|---|---|---|
| DE | 4136540 A1 | 5/1992 |
| EP | 0 297 828 A1 | 1/1989 |
| EP | 400546 | 12/1990 |
| EP | 0 564 307 A1 | 10/1993 |
| EP | 0 631 768 A1 | 1/1995 |
| EP | 0 692 263 A2 | 1/1996 |
| EP | 0 776 654 A1 | 6/1997 |
| FR | 2714603 | 7/1995 |
| GB | 2033751 A | 5/1980 |
| JP | 61-028078 | 2/1986 |
| JP | HEI 2 31756 | 2/1990 |
| JP | 04-182423 | 8/1992 |
| JP | 05-285170 | 11/1993 |
| JP | 08-52175 | 2/1996 |
| WO | WO 98/55158 | 12/1998 |
| WO | WO 00/38625 | 7/2000 |
| WO | WO 00/38626 | 7/2000 |
| WO | WO 00/38747 | 7/2000 |

* cited by examiner

PROCESS FOR APPLYING A STABLE SKIN CARE COMPOSITION TO A SUBSTRATE

CROSS REFERENCE TO RELATED APPLICATION

This is a divisional of prior copending U.S. application Ser. No. 10/417,459, filed on Apr. 16, 2003, now U.S. Pat. No. 6,793,930, which is a continuation of prior copending U.S. application Ser. No. 09/563,638, filed on May 2, 2000, now U.S. Pat. No. 6,570,054, which is a continuation-in-part of prior copending U.S. application Ser. No. 09/316,691, filed on May 21, 1999, now abandoned.

BACKGROUND OF THE INVENTION

Many types of disposable absorbent products, such as diapers, training pants, adult incontinence devices, sanitary napkins, panty liners, and the like, are available that have a high capacity for absorbing urine and other body exudates. Disposal products of this type generally comprise some sort of liquid-pervious topsheet material, an absorbent core, and a liquid-impervious backsheet material. Although these types of absorbent articles may be highly efficient for the absorption of liquids, it is generally known that skin under the absorbent article is more susceptible to skin disorders, including diaper rash or diaper dermatitis, erythema (i.e., redness), heat rash, abrasion, pressure marks and skin barrier loss. Diaper rash is a common form of irritation and inflammation of those parts of an infant's body normally covered by a diaper. It is generally accepted that diaper rash or diaper dermatitis is a condition which begins as a contact irritant dermatitis. The commonly known factors linked to diaper dermatitis include ammonia, bacteria, products of bacterial action, urine pH, *candida albicans*, and moisture. This irritation and/or inflammation result from extended contact of the skin with urine, feces, or both. When absorbent articles are worn to catch and hold the body exudates, the absorbent articles not only hold the skin of the wearer in direct contact with irritants in the body exudates, but also hold the skin in an occluded condition. Often, the skin is subjected to such a condition for extended periods of time, that is, until the soiled article is changed. As the skin under the absorbent article becomes overhydrated or irritated by such prolonged and repeated exposures, the skin condition is compromised, i.e., the skin is injured and/or becomes more susceptible to skin disorders or damages. While this condition is certainly more common in infants, it is not limited to infants. Similar conditions occur in, for example, incontinent or bed-ridden adults.

Common approaches to the improvement of skin conditions in the diapered areas often focus on reducing skin hydration, such as frequent changing of diapers, using moisture absorbing powders, using superabsorbent materials, and improving air flow in diapers, and the like.

Another common approach is to apply a topical cream, ointment, lotion or paste to the affected areas. This procedure usually provide some degree of physical barrier protection to the skin against direct contact with fecal or urine irritants. However, the barrier approach may be occlusive in itself, thus not very effective once a full blown case of diaper dermatitis has developed. There is a tendency to slather on a thick layer of the diaper rash cream or ointment, which is occlusive, messy, wasteful and aesthetically displeasing. Moreover, the excess cream/ointment may transfer to the absorbent article or other clothing, such as underwear, leading to reduced absorbency or stained clothing. This procedure is also time-consuming and often forgotten. Furthermore, the cream/ointment typically comes in a reusable container and is hand-applied to the skin. The composition often has a thick, greasy and tacky consistency in order to remain on the infant's skin, the residual composition is not easily removed from the opening of the container or the hands of the care-giver, and the possibility of cross contamination between one infant to another is increased.

An alternative approach attempts to simultaneously address multiple causes or important cofactors by using a multi-ingredient skin care composition. The composition may include barrier substances, skin conditioning agents or emollients, and may even include various skin care ingredients.

The skin care ingredients may exist as insoluble particles suspended in the substantially oleagineous compositions due to their limited solubility in the oleagineous substances. Furthermore, these solid particles generally have densities much higher than the oleagineous matrix that they are dispersed in. For example, common commercial diaper rash creams or ointments comprise zinc oxide particles dispersed in an organic matrix. Zinc oxide has a density of about 5.7 $g/cm^3$ while the density of organics is generally about 0.9 $g/cm^3$. This large difference in densities often leads to separation and processing problems.

A good suspension of the skin care ingredients in the lotion composition is highly desirable. As used herein, a "good" suspension means the particulate substances are substantially uniformly dispersed in the medium, and the dispersion is stable, i.e., no visible stratification, agglomeration or settling with the passage of time. Uniform distribution of the ingredients minimizes variation in product quality and assures that every application of the product to the skin delivers a sufficient amount of ingredients to achieve efficacy. There is no need to over-apply the product in order to achieve the desired benefits; consequently, there is less waste. Therefore, a good suspension provides the most efficient delivery of these skin care ingredients to the skin and maximizes the skin benefits. Moreover, there is no need to incorporate an extra amount of the costly ingredients to ensure efficacy; thus, an effective composition can be made at lower cost. Additionally, a good suspension also reduces the lumpiness of the lotion and provides a smooth skin feel when applied.

Generally, a suspension of particulates in a Newtonian fluid follows the Stokes law, which states that the rate of separation or settling is proportional to the density difference between the suspended particles and the suspending medium, to the square of the particle size of the suspended particles, and is inversely proportional to the viscosity of the medium. Agglomeration and gravitational settling are often observed when particulate materials are suspended in a Newtonian fluid, causing problems in storage, transportation and processing of these compositions. Where a batch process is used, the agglomeration and settling can occur in a holding tank. Moreover, as the composition flows through processing equipment, the agglomerates, formed either in the holding tank or along the process, tend to get hung up in various elements having small diameters (such as pipes, valves, slots) along the processing line. This "bridging" problem often causes clogged orifices, openings, slots and/or narrow pipes, and can severely reduce or even stop the flow of the composition through the processing equipment.

Agitation or turbulent flow can redisperse the suspended particles and avoid agglomeration and settling problems. It is known that the flow of a liquid through a pipe or like elements may be laminar or turbulent, and the transition from a laminar flow to a turbulent flow depends on the properties of the fluid, its velocity and the diameter of the pipe. However, agitation, velocity and pipe diameter are processing parameters that are constrained to a limited range for a given piece of equipment. Variations of these parameters within the equipment-limiting range often fail to solve the problem.

A variety of rheological agents, such as thickeners, thixotropic agents and dispersing agents, can be added to such a composition to alter the theological properties of the composition. These rheological agents serve to improve the stability of the suspensions and to maintain the viscosity at a desired level for a wide range process conditions and end-use situations.

Creams or ointments containing particles of zinc oxide, anti-microbials, or protease or enzyme inhibitors are known. These compositions have traditionally been prepared as oil-in-water or water-in-oil emulsions. These emulsions are not very effective in improving the condition and/or appearance of the diapered skin, particularly when the composition is delivered via a vehicle such as an absorbent article. The absorbent core element may draw the aqueous phase away from the surface of the article thereby reducing the skin benefits provided by the composition. Additionally, the oil phase, being pulled along, may interfere with the absorbency of the core. Anhydrous compositions are also known, which typically include volatile liquid carriers, such as silicone or solvents. The volatile materials can cause irritation or burning to the skin and these effects are especially acute when skin is already injured or compromised due to chronic exposure to body exudates. Moreover, the vapors from the volatile materials can become entrapped between the skin and the absorbent article worn close to the skin, further exacerbating the irritation or burning effects. Exemplary creams or ointments are disclosed in U.S. Pat. No. 4,556,560 issued Dec. 3, 1985 to Buckingham; U.S. Pat. No. 5,091,193 issued Feb. 25, 1992 to Enjolras et al.; U.S. Pat. No. 5,110,593 issued May 5, 1992 to Benford; U.S. Pat. No. 5,362,488 issued Nov. 8, 1994 to Sibley et al.; and U.S. Pat. No. 5,618,522 issued Apr. 8, 1997 to Kaleta et al.

Products containing the FDA monographed skin care ingredients are commercially available, such as A and D® Ointment, Vaseline® Petroleum Jelly, Desitin® Diaper Rash Ointment and Daily Care ointment, Gold Bond® Medicated Baby Powder, Aquaphor® Healing Ointment, Baby Magic® Baby Lotion, Johnson's Ultra Sensitive Baby Cream. These commercial products have a major disadvantage that they are creams or ointments, i.e., they are flowable at room temperature such that they can not be immobilized on the surface of an absorbent article and interfere with the absorbency of the article.

It is also known that solid or semi-solid compositions can be provided by using either solidifiable carriers or hardeners (e.g., petrolatum, waxes). For example, U.S. Pat. No. 5,194,261 issued Mar. 16, 1993 to Pichierri. The Pichierri reference discloses a semi-solid which functions as a thick, adhesive and barrier layer over the skin. The ointment has a thick and sticky consistency. An additional barrier layer is applied over the ointment. The major disadvantage of Pichierri reference is stickiness and the occlusiveness of the ointment and the barrier layer. Moreover, it does not contain the skin care ingredients of the present invention, nor the theological agent to suspend the skin care ingredients and to prevent settling. U.S. Pat. No. 4,911,932 issued Mar. 27, 1990 to Clum et al. The Clum reference teaches compositions containing specific imidazole derivatives and zinc oxide. The Clum reference does not disclose automatic transfer (i.e., without manual application) of the composition to the skin, nor a delivery vehicle for the composition, nor how to successfully dispose the composition and immobilize it on the skin-contacting surface of the delivery vehicle.

Articles treated or impregnated with skin care compositions are also known. For example, U.S. Pat. No. 3,896,807 issued Jul. 29, 1975 to Buchalter discloses an article impregnated with a solid oil phase of cream formulation which forms a cream upon addition of moisture thereto. A major disadvantage of the article disclosed by the reference is that transfer of a beneficial substance from the absorbent substrate to skin is delayed and is only realized when body fluids are released. Additionally, the reference composition does not contain skin care ingredients for skin care benefits nor rheological agents to suspend them and to prevent them from settling. U.S. Pat. No. 5,525,346 issued Jun. 11, 1996 to Hartung et al. discloses an absorbent article having oil-in-water emulsions comprising a non-ionic emulsifier, a dimethicone, sodium citrate/citric acid buffer system, aloe vera, preservatives and water. The major disadvantage of the reference that the aqueous phase may be drawn away from the surface by the absorbent element of the article, resulting in reduced effectiveness of the emulsions for skin benefits and interference with the absorbency of the article. U.S. Pat. No. 5,643,588 issued Jul. 1, 1997 and U.S. Pat. No. 5,635,191 issued Jun. 3, 1997, both to Roe et al., U.S. Pat. No. 5,607,760 issued Mar. 4, 1997, and U.S. Pat. No. 5,609,587 issued Mar. 11, 1997, both to Roe, disclose disposable absorbent articles having a lotion composition disposed on the topsheet; the lotion composition comprises an emollient and an immobilizing agent. The major disadvantage of the references is that the compositions do not contain skin care ingredients of the present invention nor rheological agents to suspend them and to prevent settling. U.S. patent application Ser. No. 09/041,509, filed Mar. 12, 1998 by McOsker et al., U.S. patent application Ser. No. 09/041,232, filed Mar. 12, 1998 by Rourke et al. and U.S. patent application Ser. No. 09/041,266, filed Mar. 12, 1998 by Roe et al., disclose skin care ingredients that are incorporated into an absorbent article directly or via an delivery vehicle, wherein the skin care ingredients are either neat or in a composition. The major disadvantage of the references is that the compositions contain no rheological agent to stabilize the skin care composition and are unsuitable for the processing/converting operation.

There remains a need for an improved skin care composition which comprises skin care ingredients specifically beneficial to diapered skin, and has a desirable rheological profile over a temperature range from processing temperature to room temperature. Specifically, the composition is a stable and processable suspension at the processing temperature and it becomes solid or semi-solid when cooled. Moreover, the composition becomes a solid or semi-solid when cooled and immobilized on a substrate surface, yet it is readily transferable to skin upon contact with body heat, normal wear motion and/or friction.

It is desirable to modify the viscosity and the elastic modulus of a skin care composition with rheological agents such that the skin care ingredients remain suspended in the composition with insubstantial agglomeration, stratification and/or settling during processing, transportation and storage.

It is also desirable that the composition becomes a solid or semi-solid when cooled, and that the composition is readily transferable to the skin it contacts. Additionally, it is desirable that the composition may be efficiently and esthetically applied to the skin via a delivery vehicle such as an absorbent article.

It is further desirable to provide a process for making an absorbent article having a stable skin care composition on a skin-contacting surface of the absorbent article.

SUMMARY OF THE INVENTION

The present invention relates to an absorbent article having a stable skin care composition disposed on at least a portion of its skin-contacting surface. The skin care composition is readily transferable to the skin via normal contact, wearer motion, and/or body heat. The skin care composition contains at least one skin care ingredient imparting skin benefits to the skin upon transfer to the skin and at least one rheological agent for stabilizing the composition such that agglomeration, stratification and/or settling are minimized.

It has been found that the rheological properties of the composition can be modified with suitable rheological agents to provide a substantially stable suspension at the processing temperature such that it can be applied to a skin-contacting surface of an absorbent article in a continuous or a batch process. Suitable compositions typically have an elastic modulus of at least about 5 dynes/cm$^2$ (measured at a strain rate of 0.2%, an oscillation frequency of 10 rad/sec and a temperature of 77° C.). When cooled, the composition becomes a solid or semi-solid such that it is substantially non-flowable and remains "locked-in" on the skin-contacting surface of the absorbent article, yet it is readily transferable to a wearer's skin via contact, normal wearer's motion, and body heat.

The present invention also relates to a process for making the absorbent articles having a substantially stable skin care composition disposed thereon. The theological agent modifies the viscosity of the composition and stabilizes the composition. The substantially stable composition can be readily transported through pipes, slots, or other elements of a processing equipment without the suspended particulates settling out or building up in the equipment. The composition can remain substantially stable even in the stationary state, e.g., while in the holding tank or in storage. Furthermore, the composition can be easily applied to a surface of a substrate without the particulates plugging up the application element of the processing equipment. Additionally, the stable lotion composition can be applied to a substrate surface in a continuous or batch process to deliver a fairly constant concentration of skin care ingredients onto the substrate surface and produce products of consistent quality throughout the run.

DETAILED DESCRIPTION OF THE INVENTION

I. Definition

Figure 1:
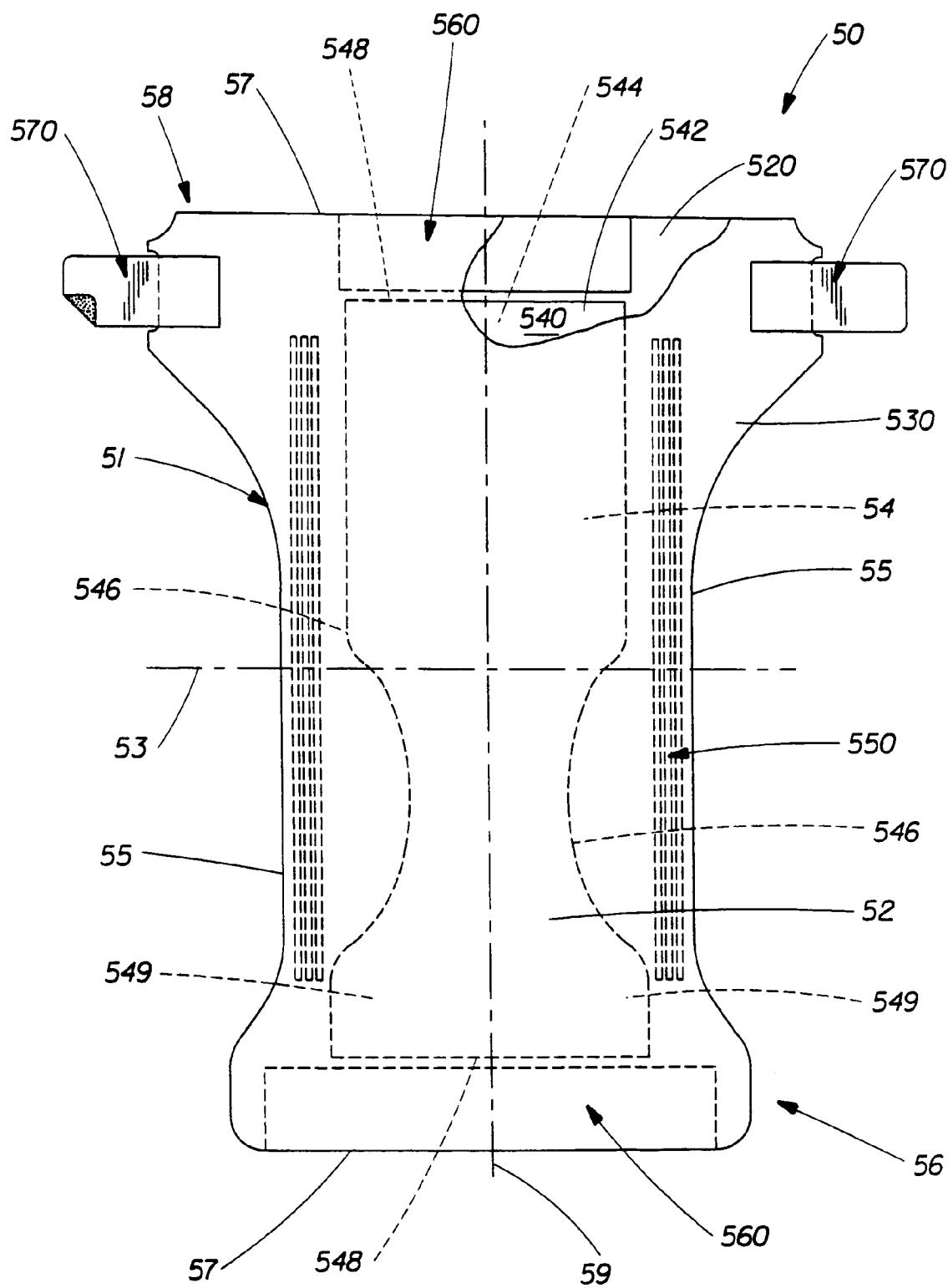
FIG. 1 is an absorbent article in the form of a diaper according to the present invention.

As used herein, the term "comprising" means that the various components, ingredients, or steps can be conjointly employed in practicing the present invention. Accordingly, the term "comprising" encompasses the more restrictive terms "consisting of" and "consisting essentially of".

As used herein, the term "skin care ingredient" means a substance or a mixture of substances, when applied to a subject's skin, either alone or incorporated into a skin care composition, provides skin benefits, directly or indirectly, such as actual or perceived changes in appearance, cleanliness and attractiveness.

As used herein, the term "effective amount" of the skin care ingredient or composition means an amount large enough to significantly or positively bring about the desired effect or to modify the condition to be treated such that the skin appears cleaner, more attractive or better overall in appearance. The effective amount varies with the specific ingredient or composition used, the preventative or prophylactic effect desired, the type of condition or disorder to be treated, the age and physical condition of the individual being treated, the severity of the condition to be treated, the intensity and duration of the treatment, and like factors.

As used herein, the terms "dermatologically acceptable" or "safe" means the amount of a skin care composition or the components therein is low enough that it produces no undue (i.e., at a reasonable benefit to risk ratio) side effects, such as toxicity, irritation, or allergic response, in a general population.

As used herein, the term "activation" of a rheological agent means the rheological agent undergoes some chemical or physical changes to form a rheological structure which effectuates the changes in theological properties of the composition.

As used herein, the term "effective amount of theological agent" means an amount of the rheological agent(s) sufficient to bring about the desired rheological properties of the composition such that the composition is stable and processable.

As used herein, the term "stable composition" or "stable suspension" means the composition or suspension shows no visible stratification, phase separation or settling for at least about 20 minutes under stationary condition at or above its melt temperature.

As used herein, the term "substantially anhydrous" means the skin care composition or the carrier typically contains 10% or less free water, preferably 5% or less free water, more preferably 1% or less free water, and most preferably 0.5% or less free water.

As used herein, the term "free water" means the water that is added in making the composition of the present invention. The term "bound water" means the water found naturally occurring in certain ingredient/component and before it is mixed with other components to make the composition of the present invention. A person of ordinary skill in the art would recognize that once the components are mixed in a composition, water can no longer be distinguished by its origin.

As used herein, the term "semisolid" means that the composition has a rheology typical of pseudoplastic or plastic liquids. When no shear is applied, the compositions can have the appearance of a semi-solid but can be made to flow as the shear rate is increased. Without intending to be bound by theory, it is believed that while the composition contains primarily solid components, it also includes some liquid components.

As used herein, the term "skin-contacting surface" or "wearer-contacting surface" of an absorbent article is one or more surfaces of any article components that may contact the wearer's skin or body at some time while the article is worn. Skin or body contacting surfaces include, but are not limited to, portions of the topsheet, the backsheet, secondary layers underlying the topsheet or the absorbent core, leg cuffs, waist regions, side panels, liners, and the like.

Other terms are defined herein where initially discussed.

All percentages, ratios and proportions used herein are defined by weight unless otherwise specified.

II. Skin Care Compositions

The skin care compositions are directed to maintain and/or improve the skin appearance and/or condition of the areas under the absorbent article or other conditions susceptible to diaper dermatitis. It is preferred that the skin care composition should provide a protective, non-occlusive function (e.g., a relatively liquid impervious but vapor pervious barrier) to avoid skin overhydration and skin exposure to materials contained in body exudates; an abrasion minimizing function to reduce skin irritation in the areas where the absorbent article is in contact with the wearer's skin; or contains ingredients that deliver, either directly or indirectly, skin care benefits. For example, the direct benefits may be directed towards redness reduction or anti-inflammatory action. The indirect benefits may be directed towards removal or reduction of skin irritants in urine or feces, or reduction in overhydration of the skin. It is also preferred that the skin care composition contains emollients or other skin care ingredients that protect or improve the skin condition against chaffing, overhydration or itchiness. Furthermore, the skin care composition preferably has a smooth, silky, non-grainy skin feel to minimize abrasion of sensitive or compromised skin having chronic conditions such as chaffing, dryness, or rashes.

The stable skin care composition of the present invention comprises a substantially anhydrous, oil-based carrier comprising an emollient and, optionally, an immobilizing agent, at least one skin care ingredient, and at least one theological agent. The skin care ingredients of the present invention may be insoluble or partially soluble solids in the substantially anhydrous, oil-based carrier. It is to be understood that oil-soluble skin care ingredients, such as Vitamins A, D, E and K, and the like, are also within the scope of the present invention. The skin care ingredients may be incorporated into the composition, either directly or as a predispersion, with agitation.

A skin care composition of the present invention has the following characteristics: first, the composition should be a stable suspension in its melt form in order to be consistently applied to a substrate surface, such as the topsheet of an absorbent article; such a stable liquid composition is substantially free from excessively large agglomerates (e.g., greater than about 1000 microns), resulting in minimal bridging and separation/settling effects, and an enhanced smooth skin feel; second, the composition should be solid or semi-solid at room temperature (i.e., 20° C.) so that there is little "migration" on the substrate surface and the adverse effect to the absorbency of the article is minimized; third, the composition is readily transferable to the skin by contact, normal wear motions and/or body heat; and fourth, the composition is preferably plastic or fluidy at skin temperature (i.e., 34° C.–36° C.) to facilitate the transfer to the skin.

The skin care compositions of the present invention are substantially anhydrous. The anhydrous nature of the composition avoids overhydration of the already susceptible skin that has been chronically exposed to a high relative humidity micro-environment. Furthermore, the anhydrous nature of the composition avoids the wicking effect of the highly absorbent diaper core, which may preferentially draw the composition towards the core, interfering with the absorbency of the core and keeping the composition away from the topsheet surface and the wearer's skin.

The compositions suitable for incorporating skin care ingredients and rheological agents therein to practice the present invention are described in U.S. patent application Ser. Nos. 08/926,532 and 08/926,533, each filed on Sep. 10, 1997; U.S. Pat. No. 5,607,760 issued Mar. 4, 1997; U.S. Pat. No. 5,609,587 issued Mar. 11, 1997; U.S. Pat. No. 5,635,191 issued Jun. 3, 1997; and U.S. Pat. No. 5,643,588 issued Jul. 1, 1997, the disclosures of each of which are hereby incorporated by reference.

One aspect of the present invention is to use rheological agents for suspending the skin care ingredients and maintaining a stable suspension. The carrier without the theological agents exhibits typical Newtonian fluid characteristics, that is, the dispersed particles, upon standing, frequently agglomerate and separate from the carrier. This drawback can lead to settling and bridging effects during processing and failure to apply the skin care composition to a substrate surface consistently. The rheology of the composition in its melt phase may be modified by an effective amount of the rheological agent(s) such that it behaves like a plastic or pseudoplastic fluid. The resultant composition is a stable solution or suspension having finely dispersed skin care ingredients therein. The stabilized composition is substantially free of agglomeration, stratification and/or settling; therefore, the melt composition can flow through processing equipment easily and be consistently applied to a substrate surface. It is found that both the elastic modulus and the apparent viscosity of the composition are factors affecting the processability of the composition.

Not intending to be bound by theory, it is believed that the elastic modulus relates to the stability of the composition and the apparent viscosity relates to the flowability of the composition. Specifically, the elastic modulus relates to the incomplete dissipation of the energy (such as shear or mixing energy) put into the composition during mixing. It is believed the residual energy stored within the composition helps to keep the particulates suspended and the components in a mixed state, i.e., the composition is stabilized. It is also believed that the apparent viscosity of the composition should not be so high such that it may lead to integrity failure (such as tearing) of the substrate surface, as well as dosing instability (i.e., non-uniform or discontinuous application of the composition to substrate surface).

Specifically, the theological agent preferably increases the elastic modulus of the composition to at least about 5 dyne/cm$^2$ when measured at 77° C. under an oscillation frequency of 10 rad/sec and a shear strain of 0.2% (see Test Method disclosed herein). Preferably the melt composition has an elastic modulus in the range from about 5 to about 50,000 dyne/cm$^2$, more preferably from about 10 to about 25,000 dyne/cm$^2$, even more preferably from about 50 to about 10,000 dyne/cm$^2$, and most preferably from about 100 to about 3,000 dyne/cm$^2$. The apparent viscosity of the composition containing the theological agent should be in the range from about 1 to about 100,000 centipoise, preferably from about 5 to about 50,000 centipoise, and more preferably from about 10 to about 5,000 centipoise, when measured under the same conditions.

As will be discussed hereinafter, the skin care compositions useful in the present invention preferably have a melting profile such that they are relatively immobilized and localized on the wearer-contacting surface of the article at room temperature, are readily transferable to the skin, and yet are not completely liquid under extreme storage conditions. Preferably, the compositions are easily transferable to the skin by way of contact, shear, normal wearer's motions and/or body heat. Because the composition preferably is substantially immobilized on the article's surface, a relatively low level of composition is needed to impart the desired skin care benefits. In addition, special barrier or wrapping materials may be unnecessary in packaging the treated articles useful in the present invention.

The preferred compositions are solid, or more often semi-solid at room temperature, i.e., at 20° C. Being solid or semi-solid at room temperature, the preferred compositions do not have a tendency to flow and migrate to a significant degree to undesired locations of the article, and thus avoid significant interference with the absorbency of the article. This means less skin care composition is required for imparting desirable appearance, protective or conditioning benefits. Preferably, the compositions of the present invention have a zero shear viscosity at room temperature between about $1.0 \times 10^6$ centipoise and about $1.0 \times 10^8$ centipoise. More preferably, the zero shear viscosity is between about $5.0 \times 10^6$ centipoise and about $5.0 \times 10^7$ centipoise.

To enhance the immobility of the preferred compositions, the viscosity of the formulated compositions should be as high as necessary to prevent substantial flow within the article to undesired location. One the other hand, too high a viscosity may inhibit transfer of composition to the skin. Therefore, a balance should be achieved so the viscosities are high enough to keep the compositions localized on the surface of the article, but not so high as to impede transfer to the skin. In addition, the compositions preferably have a final melting point above skin temperature, more preferably above potential "stressful" storage conditions that can be greater than 45° C. (e.g., warehouse in Arizona, car trunk in Florida, etc.). Specifically, preferred compositions will have the following melt profile:

| Characteristic | Preferred Range | Most Preferred |
|---|---|---|
| wt % liquid* at room temp. (20° C.) | 2–60 | 3–40 |
| wt % liquid* at body temp. (37° C.) | 25–95 | 30–90 |
| final melting point (° C.) | ≧38 | ≧45 |

*wt % of the composition excluding insoluble particles such as skin care ingredients or rheological agents.

Skin Care Ingredients

Various skin care ingredients may be incorporated into the skin care compositions provide various skin benefits, such as reduction in redness, improvement in skin appearance and/or condition, formation of a barrier or protective layer, or reduction of irritants in body wastes. A host of skin care ingredients can be incorporated into a carrier and applied to the skin. These skin care ingredients include, but are not limited to, barrier substances (petrolatum), skin conditioning agents (oil, lanolin), proton donating agents, protease and/or enzyme inhibitors, and antimicrobials. The skin care composition may also contain humectants (glycerine, sorbitol), vitamins, skin soothing agents, such as aloe vera, or other ingredients from herbal, botanical or mineral sources, or multi-functional agents, such as zinc oxide.

A wide variety of topically effective ingredients can be incorporated into the stable composition of the present invention. Such skin care ingredient provides visible benefits to the occluded skin under an absorbent article when applied according to the present invention. The skin care ingredients can be uniformly dispersed throughout the composition as insoluble particulates. Alternatively, the skin care ingredients can be solubilized in the substantially anhydrous carrier of the present invention. The resultant composition is substantially stable (i.e, resistant to excessively large agglomeration, stratification and/or settling), has a solid or semi-solid consistency at room temperature that renders it readily transferable to the skin, and is suitable for topical application to the skin via a delivery vehicle such as an absorbent article or elements thereof.

Numerous materials that have been deemed safe and effective skin care ingredients are logical materials for use herein. Such materials include Category I and Category III actives as defined by the U.S. Food and Drug Administration's (FDA) Tentative Final Monograph on Skin Protectant Drug Products for Over-the-Counter Human Use (21 C.F.R. § 347). It will be recognized that several of the monographed actives listed below are "emollients" as defined herein. Category I actives presently include: allantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Category III actives presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, and the like. These monographed materials are known to provide multiple skin benefits, such as skin protectant, itch prevention, irritation prevention, via various mechanisms.

The skin care ingredients suitable for the present invention may also include, but are not limited to, pH control agents or proton donating agents, such as pH buffer systems, ammonium-neutralizing agents, organic acids, polymeric acids, inorganic acids, and their salts; anti-microbials; enzyme inhibitors; protease inhibitors; anti-coenzymes; chelating agents; and anti-bodies. Some nonlimiting examples of proton donating agents are described in U.S. application Ser. No. 09/041,509, by McOsker et al. filed on Mar. 12, 1998.

Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases. Some non-limiting examples of such protease inhibitors are described in U.S. application Ser. No. 09/041,232, by Rourke et al filed on Mar. 12, 1998, U.S. Pat. No. 5,091,193 issued to Enjolras et al, on Feb. 25, 1992, and U.S. Pat. No. 4,556,560 issued to Buckingham on Dec. 3, 1985, all are incorporated by reference herein.

Enzyme inhibitors are designed to inhibit specific enzymatic activities of various classes of proteases. Specifically useful for the present invention are inhibitors that interact with those proteolytic and lipolytic enzymes commonly present in feces, such as lipases, esterases, diesterases, ureases, amylases, elastases, nucleases, The enzyme inhibitors suitable for use in the present invention include, but are not limited to, chelating agents which bind to metal cofactors of specific enzymes, antibodies raised for specific enzymes, enzyme inhibitors for various enzymes or coenzymes, preferably of the proteolytic type, such as trypsin, chymotrypsin, aminopeptidase and elastase, serine, cysteine, lipases, bile salts (acting as coenzymes that enhance the activities of lipases), amylases, and/or ureases. Other enzyme inhibitors known to effectively reduce or interfere with enzyme activities are also contemplated to be within the scope of the present invention. Some non-limiting examples of such enzyme inhibitors are described in U.S. application Ser. No. 09/041,266, by Roe et al. and U.S. application Ser. No. 09/041,196, by Underiner et al., both filed on Mar. 12, 1998, U.S. Pat. No. 5,376,655 issued to Imaki et al. on Dec. 27, 1994, U.S. Pat. No. 5,091,193 issued to Enjolras et al. on Feb. 25, 1992, U.S. Pat. No. 3,935,862 issued to Kraskin on Feb. 3, 1976, U.S. Pat. No. 5,409,903 issued to Polak et al. on Apr. 25, 1995, U.S. Pat. No. 4,556,560 issued to Buckingham on Dec. 3, 1985, Patent Application EP 97/120,699 and EP 97/120,700 both by Palumbo et al. and filed on Nov. 26, 1997, all are incorporated by reference herein.

The skin care ingredients in the present invention should preferably include at least one of the following: zinc oxide, talc, starch, allantoin, hexamidine and its salts and derivatives, hexamidine diisethionate, and its salts, triacetin, phytic acid, ethylenediamine tetraacetic acid (EDTA), and 4-(2-aminoethyl)-benzenesulfonylfluoride hydrochloride, chitosan, and mixtures thereof.

Generally, a safe and effective amount of a skin care ingredient is incorporated into the composition. The skin care compositions suitable for the present invention may contain skin care ingredients in a concentration of from about 0.001% to about 70% by weight, preferably from about 0.01% to about 45%, more preferably from about 0.1% to about 25%, and most preferably from about 0.1% to about 10%. The skin care ingredients may be used singly or as a mixture of skin care ingredients in a "cocktail". Because of the variety of skin care ingredients that may be used in the present invention, the effective concentration of each skin care ingredient should be separately determined, as known to those skilled in the art.

Where the ingredients are insoluble in the composition, the average particle size of the ingredients plays an important role in suspending the particles in the composition without substantial agglomeration, stratification and/or settling. The particles should be substantially free of excessively large agglomerates, i.e., there is negligible amount of particles larger than 1000 microns. The average particle size of the skin care ingredients should preferably be less than about 1000 microns, more preferably less than about 100 microns, and most preferably less than about 50 microns.

It is generally known that solid particles in neat form tend to form clumps or agglomerates, bound by static charges, interactions between functional groups, etc. It is often necessary to break up the clumps in order to disperse the particles, to reduce the settling effect, and to deliver skin benefits effectively. The break-up and dispersion can be accomplished by grinding or milling, by incorporation into a composition with agitation, by predispersing in a dispersant mixture, by predissolving in a carrier or by other methods known to persons skilled in the art.

The predispersant mixture preferably comprises a dispersant fluid and optionally, a wetting agent. The wetting agent is typically a surfactant having a hydrophilic end, which interacts with the functional groups on the surface of the ingredient particles, and a lipophilic end, which is compatible with the oil-based carrier of the present composition. Without intending to be bound by theory, it is believed that the wetting agent, along with external forces applied (such as shear, agitation), facilitates the break-up of the clumps of the skin care ingredients and the mixing or dispersion of the particulate ingredients in the composition. It is also believed that the wetting agent, being a hydrophilic-lipophilic, surfactant-type material, bridges the interfaces between the particulate ingredients and the substantially anhydrous carrier. It is also believed that the dispersant fluid can serve as a diluent and/or a wetting agent for predispersing the particles. Additionally, the dispersant fluid preferably is miscible with the substantially anhydrous, oleaginous composition of the present invention. Nonlimiting examples of the dispersant fluid include mineral oil, dimethicone and other silicones, esters, preferably the condensation products of $C_1$–$C_{22}$ alcohols with $C_1$–$C_{22}$ acids. The predispersion preferably has a high solid or particle content in the range of 50% to 99% by weight solids, more preferably from 60% to 90% by weight solids, and most preferably from 70% to 80% by weight solids. Various grinding and/or milling techniques known in the art are sometimes used in the predispersing process to break down the particle size and disperse the particles.

In a preferred embodiment, the ingredient is zinc oxide dispersed, as insoluble particles, in the oleaginous, substantially anhydrous carrier of the present invention. More preferably, the zinc oxide particles are prepared as a predispersion. The skin care composition comprises from about 1 wt % to about 70 wt % of the zinc oxide predispersion, preferably from about 3 wt % to about 50 wt %, more preferably from about 5 wt % to about 30 wt %. The predispersion has preferably from about 90 wt % to about 50 wt % zinc oxide, from about 1 wt % to about 50 wt % dispersant fluid and from about 0.1 wt % to about 10 wt % wetting agent. A preferred embodiment comprises about 75 wt % zinc oxide particles dispersed in about 22 wt % of a dispersant fluid such as those described above and about 3 wt % of a polyglyceyl ester wetting agent. Suitable zinc oxide predispersion is available from Kobo Products, Inc., S. Plainfield, N.J. The zinc oxide particles of the present invention typically consist of agglomerates of primary particles. The particle size of the agglomerates ranges from about 0.1 to about 300 microns and the average agglomerate size is about 1.0 microns. The average particle size of the primary particles is about 0.12 microns. Typically the agglomerate comprises about 5 to about 8 primary particles.

Alternatively, a hydrophobic modification can be applied to the zinc oxide particles to "wet" the surface of the particles. In this process, surfactants are actually attached to the surface of the zinc oxide particles under high temperature or pressure. The modified or "wetted" zinc oxide particles with the lipophilic ends of the surfactants extending from their surfaces, become at least partially miscible in the oil-based carrier of the present compositions.

Rheological Agents

The rheological agents should provide sufficient modification to the rheological properties of the compositions to be able to maintain relatively stable suspensions of skin care active particles therein. Because the present compositions are complex mixtures of components, the modifications of the theological properties operate under complex interactions and mechanisms. It is found that the stability and processability of a composition relate to the elastic modulus and apparent viscosity of the composition in the melt form.

It is found that the elastic modulus of the composition in the melt (measured at the melt processing temperature of about 77° C.) correlates with the stability and processability of the composition. A substantially stable and processable composition in the melt should have an elastic modulus of at least about 5 dynes/cm$^2$, as measured according to the Test Method disclosed herein. The preferred elastic modulus of such a composition is in the range of about 5 to about 50,000 dynes/cm$^2$, preferably from about 10 to about 25,000 dynes/cm$^2$, more preferably from about 50 to about 10,000 dynes/cm$^2$, and most preferably from about 10 to about 3,000 dynes/cm$^2$, as measured according to the Test Method disclosed herein.

The apparent viscosity of the composition is characterized by measurements at 0.1 rad/sec at two temperatures including the processing temperature and the "stressful" storage temperature (or about 45° C.). The apparent viscosity of the melt composition is preferably from about 1 centipoise to 100,000 centipoise, more preferably from about 5 centipoise to about 50,000 centipoise, and even more preferably from about 10 centipoise to about 5,000 centipoise.

The unmodified (i.e., in the absence of added rheological agents) melt composition exhibits substantially Newtonian fluid characteristics, which are known to result in agglomeration, stratification and/or settling of the suspended particles. Consequently, bridging and clogging of the processing equipment may occur. According to the present invention, an effective amount of one or more rheological agents are added to the composition to change the rheological properties of the melt composition to a plastic or pseudoplastic fluid, which is generally stable and processable in standard equipment. The term "stable", as used herein, means the composition (having the skin care ingredients dispersed/suspended in the carrier) shows no visible stratification or significant phase separation for at least about 20 minutes, preferably for at least about 4 hours, and more preferably at least about 8 hours, under stationary condition at or above melt temperature.

The rheological agents can be insoluble or partially soluble particles in the oil-based, substantially anhydrous carrier of the present invention. These particulate theological agents are typically in the form of finely divided, small particles having an average particle size less than about 100 microns and a solubility in the composition of less than 10%, preferably less than 5% by weight. However, the particle size may vary, depending on type of agent, the mechanism to provide rheological effects, the activation or preparation of the theological agent, and other like factors. It is also recognized that the theological agents need not be solid particles in the carrier. That is, the theological agents may be miscible or partially miscible with the carrier. It is recognized that the rheological agents may function as immobilizing agents or hardeners as well. It is also recognized that the theological agents may be incorporated into the composition singly or as mixtures of various theological agents.

The preparation and/or activation of the theological agents may involve, but is not limited to, the following steps: reduction in agglomerates by milling, grinding, agitation or other methods known in the art; and activation by methods known in the art, such steps being dependent upon the type of theological agent used.

Some rheological agents may also function as hardeners or immobilizing agents to provide a solid or semi-solid composition at room temperature (i.e., about 20° C.). That is, rheological agents may be added to the composition such that the composition is hardened and/or immobilized sufficiently on the substrate surface, while not substantially interfering its transferability to the skin that comes into contact with the composition.

The rheological agents comprises from about 0.1% to about 25% by weight of the total composition, preferably from about 0.25% to about 10% by weight, and more preferably from about 0.5% to about 5% by weight of the total composition.

Type A Rheological Agents

A skin care composition modified by this type of theological agents typically exhibits a substantially "flat" rheological profile with respect to temperature. Specifically, the apparent viscosity of the composition does not change substantially over the temperature range from about the processing temperature to room temperature. An immobilizing agent may be added to produce a solid or semi-solid composition at room temperature.

A preferred rheological agent for use herein is fumed silica, either surface-treated or untreated. The untreated fumed silica is available commercially under the trade name CAB-O-SIL M-5 and HS-5, by Cabot Corporation, Tuscola, Ill. More preferred for use herein is surface-treated fumed silica. Even more preferred is a fumed silica selected from the group consisting of polyalkylsiloxane treated fumed silica, trialkylsilanized fumed silica, dialkylsilanized fumed silica, and mixtures thereof. Most preferred is a fumed silica selected from the group consisting of polydimethylsiloxane treated fumed silica, trimethylsilanized fumed silica, dimethyldisilanized fumed silica, and mixtures thereof.

The fumed silica and treated fumed silica generally exist as agglomerates in the composition with a volume weighted average particle size of from about 0.001 micron to about 100 microns, preferably from about 0.005 micron to about 50 microns, and more preferably from about 0.01 microns to about 10 microns. The agglomerated configuration is the most efficient for interparticle interactions, which form the network structure that thickens and stabilizes the suspension.

The fumed silicas typically have active hydroxyl groups, and it may be desirable to treat these fumed silicas such that the characteristics of the hydroxyl groups are altered. A useful method of treatment is to coat the fumed silicas with a nonpolar organic compound such as polyalkylsiloxanes, preferably a polydimethylsiloxane, to render the hydroxyl groups less active. A polydimethylsiloxane treated fumed silica useful herein is available commercially under the trade name CAB-O-SIL TS-720, by Cabot Corporation, Tuscola, Ill. Another useful method of treatment is to chemically react the hydroxyl groups of the fumed silica with a silanizing agent, e.g., dimethyldichlorosilane or hexamethyldisilizane. The chemically treated fumed silicas have the free hydroxyl groups replaced with an oxygen-silicon bond of the silanizing agent. A trimethylsilanized fumed silica useful herein is available commercially under the trade name CAB-O-SIL TS-530, and a dimethylsilanized fumed silica useful herein is available commercially under the trade name CAB-O-SIL TS-610, both by Cabot Corporation, Tuscola, Ill.

Also useful herein are organoclays, such as bentonites and hectorites that preferably have been treated (i.e., coated) with various organic compounds to render the clays less polar. These organoclays are typically made from a smectic clay platelet having a fatty chain organic compound bonded to its faces, and leaving the edges free to form hydrogen bonds. The fatty chains provide dispersibility in the substantially anhydrous, oil-based composition, while the edge-to-edge hydrogen bonding of the platelets provides suspension stability. Nonlimiting examples include quaternium-18 hectorites, stearalkonium hectorites, quaternium-18 bentonites, quaternium-18 benzalkonium bentonites, stearalkonium bentonites, and their mixtures with at least one member selected from the group consisting of with mineral oil, propylene carbonate, isopropyl palmitate, cyclomethicone, caster oil, lanolin, propylparaben, and C12–C15 alkyl benzoate. These organoclays or mixtures are available from Rheox, Inc., Hightstown, N.J., under the general trade names of BENTONE and BENTONE GEL. More preferred for use herein are BENTONE 38 (a quaternium-18 hectorite), BENTONE 27 (a stearalkonium hectorite), and BENTONE 34 (a quaternium-18 bentonite).

Metal fatty ester soaps are also useful herein. Specifically useful herein are soaps made from the combination of at least one metal ion selected from the group consisting of aluminum, magnesium, zinc and lithium, and at least one fatty acid ester having a chain length of 10 to 28 carbon atoms, preferably of 12 to 22 carbon atoms, such as stearates, behenates, laurates and palmitates. More preferred for use herein are aluminum/magnesium hydroxide stearates, which are hydrophobic platelets formed from the complexation between stearic acid and aluminum/magnesium hydroxide in alternate layers. The platelet structure swells in the oil, thereby changes the rheological characteristics of the composition. Specifically, the viscosity of the composition is fairly constant over a broad temperature range. This allows for enhanced stability of the suspension over the temperature range of the present invention. The aluminum/magnesium hydroxide stearate is available from Giulini Corporation, Bound Brook, N.J., under the general name of GILUGEL.

Also useful herein are calcium silicates and treated calcium silicates. Common forms of calcium silicates include $CaSiO_3$, $CaSiO_4(OH)_2$, $CaSiO_5(OH)_4$. The calcium silicates can be treated with a wide variety of nonpolar organic compounds to render the materials more hydrophobic and less reactive. Useful calcium silicates that are commercially available include the following: HUBERSORB (Huber Corp., Harve de Grace, Md.), and MICRO-CEL (Celite Corp., Denver, Colo.). Other silicates such as magnesium silicate, or magnesium/aluminum silicate are also useful herein.

Other nonlimiting examples also useful herein are rheological agents derived from natural sources, such as cholesterol and hydrogenated lecithin, and anionic surfactants such as DEA (diethanolamide) Oleth-3 phosphate.

Type B Rheological Agents

A skin care composition modified by this type of rheological agents typically exhibit a substantially temperature-dependent rheological profile. Specifically, the apparent viscosity of the composition increases as the temperature decreases from the processing temperature to room temperature. That is, Type B rheological agent functions like an immobilizing agent. Inclusion of an additional immobilizing agent to produce a solid or semi-solid composition at room temperature is optional when Type B rheological agent is used.

Useful herein are various organic derivatives of castor oil, such as THIXCIN R, THIXATROL ST, and the like. The principal constituent of these castor oil derivative is glyceryl tris-12-hydroxystearate. Various inorganic derivatives of castor oil are also useful herein, such as THIXCIN GR, THIXATROL GST, THIXSEAL 1084, and the like. All these castor oil derivatives or mixtures thereof are available from Rheox, Inc., Hightstown, N.J.

Also useful herein are polymeric rheological agents. Nonlimiting examples are polymethacrylate polymers, polymethacrylate and styrene copolymers, which can optionally be crosslinked a common crosslinking agent, polyethylene, polyethylene and acrylic acid or vinyl acetate copolymers, polyisobutylene, poly-α-olefins, bi or tri-component copolymers of styrene and hydrogenated ethylene, propylene, butylene, and/or, Nylon 66 and hydrophobic cellulose derivatives.

Also useful herein are nonionic surfactants. Nonlimiting examples include polyethylene oxide ethers derived from $C_8$–$C_{22}$ alcohols, preferably ceteth-10 (polyoxyethylene 10 cetyl ether), steareth-21 (polyoxyethylene stearyl ether) and mixtures thereof; ethoxylated or propoxylated alcohols or alkyl phenols, having preferably $C_8$–$C_{22}$ alkyl chains and preferably from about 6 to about 25 ethylene oxide or propylene oxide groups; mono- and di- fatty acid esters of ethylene glycol; fatty acid monoglyceride; sorbitan; mono- and di-$C_8$–$C_{22}$ fatty acids; polyoxyethylene sorbitan; and mixtures thereof.

Also useful herein are waxes such as camauba, ozokerite, beeswax, candelilla, paraffin, ceresin, esparto, ouricuri, rezowax, isoparaffin, silicone waxes, polyethylene waxes, and other known mined and mineral waxes. Additionally microcrystalline waxes are also effective rheological agents. A preferred wax is a paraffin wax such as Paraffin S.P. 434 from Strahl and Pitsch Inc., West Babylon, N.Y.

Other nonlimiting examples also useful herein, without specific regard to the rheology-temperature profiles, are diethanolamides; methylethylamides; and amphoteric surfactants such as dialkylamino propionic acid; alkyl galactomannan, zinc stearate, sorbitan sesquioleate, cetyl hydroxy ethyl cellulose and other modified celluloses.

Emollients

For skin care compositions designed to provide skin appearance and/or skin protective benefits, a useful ingredient in these compositions is one or more skin protectants or emollients. As used herein, the term "emollient" means a material that protects against wetness or irritation, softens, soothes, supples, coats, lubricates, moisturizes, protects and/or cleanses the skin; the term "protectant" means a material which protects injured or exposed skin or mucous membrane surface from harmful or annoying stimuli. In a preferred embodiment, these emollients will have either a plastic or liquid consistency at room temperatures, i.e., 20° C.

Representative emollients useful in the present invention include, but are not limited to, emollients that are petroleum-based; sucrose ester fatty acids; polyethylene glycol and derivatives thereof; humectants; fatty acid ester type; alkyl ethoxylate type; fatty acid ester ethoxylates; fatty alcohol type; polysiloxane type; propylene glycol and derivatives thereof; glycerine and derivatives thereof, including glyceride, acetoglycerides, and ethoxylated glycerides of $C_{12}$–$C_{28}$ fatty acids; triethylene glycol and derivatives thereof; spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; any of the monographed skin care agents listed above; or mixtures of these emollients. Suitable petroleum-based emollients include those hydrocarbons, or mixtures of hydrocarbons, having chain lengths of from 16 to 50 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for compositions of the present invention.

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$–$C_{28}$, preferably $C_{12}$–$C_{16}$) and shorter chain fatty acids e.g., lactic acid, such as lauryl lactate and cetyl lactate.

Suitable alkyl ethoxylate type emollients include $C_{12}$–$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$–$C_{22}$ fatty alcohols, preferably $C_{16}$–$C_{18}$ fatty alcohols. Representative examples include cetyl alcohol and stearyl alcohol, and mixtures thereof. When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use herein include polysiloxane compounds. In general, suitable polysiloxane materials for use in the present invention include those having monomeric siloxane units of the following structure:

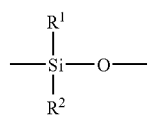

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are tolyl, xylyl, ethylphenyl, and the like. Exemplary aryl radicals are benzyl, αphenylethyl, β-phenylethyl, α-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluoroethyl, fluoroethyl, trifluoroethyl, trifluorotloyl, hexafluoroxylyl, and the like.

Viscosity of polysiloxanes useful for the present invention may vary as widely as the viscosity of polysiloxanes in general vary, so long as the polysiloxane is flowable or can be made to be flowable for application to the absorbent article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the absorbent articles by such methods as, for example, emulsifying the polysiloxane in surfactant or providing the polysiloxane in solution with the aid of a solvent, such as hexane, listed for exemplary purposes only. Particular methods for applying polysiloxane emollients to absorbent articles are discussed in more detail hereinafter.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the compositions of the present invention include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Suitable fatty ester type emollients also include polyolpolyesters as described in U.S. Pat. No. 5,609,587, issued to Roe on Mar. 11, 1997, the disclosure of which is incorporated herein by reference. Exemplary polyols include, but are not limited to, polyhydric compounds such as pentaerythritol; sugars such as raffinose, maltodextrose, galactose, sucrose, glucose, xylose, fructose, maltose, lactose, mannose and erythrose; and sugar alcohols such as erythritol, xylitol, malitol, mannitol and sorbitol. Such polyols are esterified with fatty acids and/or other organic radicals having at least two carbon atoms and up to 30 carbon atoms. While it is not necessary that all of the hydroxyl groups of the polyol be esterified, preferred polyolpolyester emollients of the present invention have substantially all (e.g., at least about 85%) of the hydroxyl groups esterified. Particularly preferred are sucrose polyolpolyesters such as sucrose polycottonate, sucrose polysoyate, and sucrose polybehenate. Mixtures of such polyolpolyesters are also suitable emollients for the present invention.

Suitable humectants include glycerine, propylene glycol, sorbitol, trihydroxy stearin, and the like.

When present, the amount of emollient that can be included in the composition will depend on a variety of factors, including the particular emollient involved, the skin benefits desired, the other components in the composition and like factors. The composition will comprise from 0 to 99.9%, by total weight, of the emollient. Preferably, the composition will comprise from about 10 to about 95%, more preferably from about 20 to about 80%, and most preferably from about 40 to about 75%, by weight, of the emollient.

Immobilizing Agent

An optional component of the skin care is an agent capable of immobilizing the composition in the desired location in or on the treated article. Because some embodiments of the composition have a plastic or liquid consistency at 20° C., they tend to flow or migrate, even when subjected to modest shear. When applied to a wearer-contacting surface or other location of an absorbent article, especially in a melted or molten state, the composition will not remain primarily in or on the treated region. Instead, the composition will tend to migrate and flow to undesired regions of the article and adversely affect the absorbency of the article.

Specifically, if the composition migrates into the interior of the article, it can cause undesired effects on the absorbency of the article. It also means that much more composition has to be applied to the article to get the desired skin smoothness benefits. Increasing the add-on level of composition not only increases the cost, but also exacerbates the undesirable effect on the absorbency of the article's core and undesired transfer of composition during processing/converting of the treated articles.

The immobilizing agent counteracts this tendency of the composition to migrate or flow by keeping the composition primarily localized on the surface or in the region of the article to which the composition is applied. This is believed to be due, in part, to the fact that the immobilizing agent raises the melting point and/or viscosity of the composition. Since the immobilizing agent is preferably miscible with the carrier/emollient (or solubilized in the carrier/emollient with the aid of an appropriate emulsifier or dispersed therein), it entraps the composition on the surface of the article's wearer contacting surface or in the region to which it is applied.

In addition to being miscible with (or solubilized in) the carrier/emollient, the immobilizing agent preferably has a melting profile that will provide a composition that is solid or semisolid at room temperature. In this regard, preferred immobilizing agents will have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

It is also advantageous to "microscopically" lock or entrap the components of the composition on the wearer contacting surface or the region of the article to which the composition is applied. This can be accomplished by using immobilizing agents which tend to form fine crystals or have high crystallinity. Upon cooling, the immobilizing agent forms multiple seeds or nuclei, from which the crystalline structures grow, and entrap other components. In addition, outside cooling of the treated article via blowers, fans, cold rolls, etc. can speed up crystallization of the immobilizing agent.

When utilized, immobilizing agents useful herein can be selected from any of a number of agents, so long as the protease-inhibiting properties of the skin care composition provide the skin benefits described herein. Preferred immobilizing agents will comprise a member selected from the group consisting of $C_{14}$–$C_{60}$ fatty alcohols, $C_{14}$–$C_{60}$ fatty acids, and $C_{14}$–$C_{60}$ fatty alcohol ethoxylate having an average degree of ethoxylation ranging from about 2 to about 110, and mixtures thereof. The alkyl chain of the fatty alcohols, fatty acids, or fatty acid esters is typically $C_{14}$ to $C_{60}$, preferably $C_{16}$ to $C_{50}$, and more preferably $C_{20}$ to $C_{40}$. The alkyl chains may be linear, branched, saturated or unsaturated, with linear chains being the preferred structure. The high melting crystalline materials are more effective as the immobilizing agents. It is believed that the long, linear structure of these materials can speed up solidification on the treated absorbent article and "lock" up the composition more rapidly. The average degree of ethoxylation is preferably from about 2 to about 40, more preferably from about 5 to about 20. In one embodiment, the immobilizing agents include $C_{16}$–$C_{18}$ fatty alcohols, such as cetyl alcohol, stearyl alcohol, behenyl alcohol, and mixtures thereof. Mixtures of cetyl alcohol and stearyl alcohol are particularly preferred. In another embodiment, the immobilizing agents include $C_{16}$–$C_{18}$ fatty acids, most preferably selected from the group consisting of palmitic acid, stearic acid, and mixtures thereof. Mixtures of palmitic acid and stearic acid are particularly preferred. Still other embodiments use immobilizing agents such as $C_{16}$–$C_{18}$ fatty alcohol ethoxylates having an average degree of ethoxylation ranging from about 2 to about 32, preferably from about 5 to about 20.

Other types of immobilizing agents that may be used herein include polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using articles to which the composition is applied, these esters and amides should also be relatively mild and non-irritating to the skin.

Suitable polyhydroxy fatty acid esters for use in the present invention will have the formula:

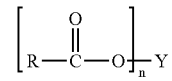

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose;

sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters and diesters are particularly preferred and include sucrose mono- and di-stearate and sucrose mono- and di- laurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 to Honsa, issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —$CH(CH_2OH)$—$[(CHOH)_{n-1}]$—$CH_2OH$, —$CH_2OH$—$CH_2$—$(CHOH)_{2-(CHOR^3)}(CHOH)$—$CH_2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

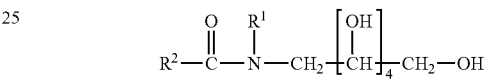

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents may require an emulsifier for solubilization in the emollient. This is particularly the case for certain of the glucamides such as the N-alkyl-N-methoxypropyl glucamides having hydrophilic lipophilic balance (HLB) values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially uniform mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes. The high melt point of these materials can help immobilize the composition on the desired surface or location on the article. Additionally microcrystalline waxes are effective immobilizing agents. Microcrystalline waxes can aid in "locking" up low molecular weight hydrocarbons within the skin care composition. Preferably the wax is a paraffin wax. An example of a particularly preferred alternate immobilizing agent is a paraffin wax such as Parrafin S.P. 434 from Strahl and Pitsch Inc., West Babylon, N.Y. Synthetic waxes such as those derived from polyethylene may also be used herein.

Depending on the rheological properties and thermal properties (especially the melting temperature) of the composition, the amount of the immobilizing agent may vary. When present, the composition typically comprises from about 5 to about 95 wt %, preferably from about 5 to about 50 wt %, most preferably from about 10 to about 40 wt %, of the immobilizing agent.

Optional Hydrophilic Surfactants

It is highly desirable that at least a portion of the article's topsheet be made of a hydrophilic material to promote rapid transfer of liquids (e.g., urine) through the topsheet. Similarly, it may be desirable that the composition be sufficiently wettable to ensure that liquids will transfer through the topsheet rapidly. Alternatively, hydrophobic skin care compositions may be utilized, so long as they are applied such that the fluid handling properties of the topsheet are adequately maintained. (For example, as discussed below, nonuniform application of the composition to the topsheet is one means to accomplish this goal.) This diminishes the likelihood that body exudates will flow off the composition-treated topsheet rather than being drawn through the topsheet and being absorbed by the absorbent core. Where a hydrophilic composition is desired, depending upon the particular components used in the composition, a hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$–$C_{18}$ fatty alcohols having HLB values below about 7 may require addition of hydrophilic surfactant to improve wettability when the composition is applied to article topsheets. Similarly, a hydrophobic emollient such as petrolatum may require the addition of a hydrophilic surfactant if a hydrophilic composition is desired. Of course, the concern around wettability is not a factor when the wearer-contacting surface under consideration is other than the article's topsheet or when fluid handling properties of the topsheet are adequately maintained via other means (e.g., nonuniform application).

Suitable hydrophilic surfactants will preferably be miscible with the other components of the skin care composition so as to form blended mixtures. Because of possible skin sensitivity of those using disposable absorbent products to which the composition is applied, these surfactants should also be relatively mild and non-irritating to the skin. Typically, these hydrophilic surfactants are nonionic to be not only non-irritating to the skin, but also to avoid other undesirable effects on any other structures within the treated article. For example, reductions in tissue laminate tensile strength, adhesive bond sufficiencies, and the like.

Suitable nonionic surfactants may be substantially non-migratory after the composition is applied to the articles and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30° C. In this regard, these nonionic surfactants will preferably have melting points similar to those of the immobilizing agents previously described.

Suitable nonionic surfactants for use in compositions that will be applied to the articles, at least in the liquid discharge region of the diaper, include alkylglycosides; alkylglycoside ethers as described in U.S. Pat. No. 4,011,389, issued to Langdon, et al on Mar. 8, 1977, which is incorporated by reference; alkylpolyethoxylated esters such as Pegosperse 1000MS (available from Lonza, Inc., Fair Lawn, N.J.), ethoxylated sorbitan mono-, di- and/or tri-esters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 8 to about 22 carbon atoms with from about 2 to about 30 moles of ethylene oxide per mole of alcohol (on average). Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$–$C_{15}$ linear alcohols with 9 moles of ethylene oxide), marketed by Union Carbide Corporation of Danbury, Conn.; the NEODOL brand name surfactants marketed by Shell Chemical Co. of Houston, Tex., in particular NEODOL 25-12 (condensation product of $C_{12}$–$C_{15}$ linear alcohols with an average of 12 moles of ethylene oxide) and NEODOL 23-6.5T (condensation product of $C_{12}$–$C_{13}$ linear alcohols with an average of 6.5 moles of ethylene oxide that has been distilled (topped) to remove certain impurities), and especially the PLURAFAC brand name surfactants marketed by BASF Corp. of Mt. Olive, N.J., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 72 (i.e., Steareth-2) and Brij 76 (i.e., Steareth-10) being especially preferred. Also, mixtures of cetyl alcohol and stearyl alcohol ethoxylated to an average degree of ethoxylation of from about 2 to about 30, preferably from about 10 to about 20, may also be used as the hydrophilic surfactant.

Another type of suitable surfactant for use in the composition includes Aerosol OT, a dioctyl ester of sodium sulfosuccinic acid marketed by Cytec Industries, Inc. of Morristown, N.J.

Still another type of suitable surfactant for use in the composition includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the composition.

Where a hydrophilic composition is desired, the amount of hydrophilic surfactant required to increase the wettability of the composition to a desired level will depend in part upon the HLB value and level of immobilizing agent, if any, used, the HLB value of the surfactant used and like factors. The composition can comprise from about 0.1 to about 50% of the hydrophilic surfactant when needed to increase the wettability properties of the composition. Preferably, the composition comprises from about 1 to about 25%, most preferably from about 10 to about 20%, of the hydrophilic surfactant when needed to increase wettability.

Other Optional Components

Compositions can comprise other components typically present in emulsions, creams, ointment, lotions, suspensions, etc. of this type. These components include water, disinfectant antibacterial actives, antiviral agents, vitamins, pharmaceutical actives, suspending agents, film formers, perfumes, deodorants, opacifiers, astringents, solvents, preservatives, and the like. In addition, stabilizers can be added to enhance the shelf life of the composition such as cellulose derivatives, proteins and lecithin. All of these materials are well known in the art as additives for such formulations and can be employed in appropriate amounts in the compositions for use herein.

If water-based skin care compositions are used, a preservative will be needed. Suitable preservatives include propyl paraben, methyl paraben, benzyl alcohol, benzalkonium, tribasic calcium phosphate, BHT, or acids such as citric, tartaric, maleic, lactic, malic, benzoic, salicylic, and the like. Suitable viscosity increasing agents include some of the agents described as effective immobilizing agents. Suitable solvents include propylene glycol, glycerine, cyclomethicone, polyethylene glycols, hexalene glycol, diol and multi-hydroxy based solvents. Nonlimiting examples of suitable vitamins include A, $D_3$, E, $B_5$ and E acetate.

III. Absorbent Article

As used herein, the term "absorbent article" refers to a device which absorbs and retains body exudates. The term "disposable" is used herein to describe absorbent articles which are not intended to be laundered or otherwise restored or reused as an absorbent article after a single use. Examples of disposable absorbent articles include feminine hygiene garments such as sanitary napkins, panti-liners and tampons, diapers, incontinence briefs, diaper holders, training pants, and the like.

Disposable absorbent articles typically comprise a topsheet (preferably liquid pervious), a backsheet (preferably liquid impervious) and an absorbent core positioned between the topsheet and the backsheet. Disposable absorbent articles and components thereof, including the topsheet, backsheet, absorbent core, and any individual layers of these components, have a body facing surface and a garment facing surface. As used herein, "body facing surface" means that surface of the article or component which is intended to be worn toward or adjacent to the body of the wearer, while the "garment facing surface" is on the opposite side and is intended to be worn toward or placed adjacent to the wearer's clothing or undergarments when the disposable absorbent article is worn.

The following description generally discusses the absorbent core, topsheet, and backsheet materials that are useful in disposable absorbent articles that are used in the methods of the present invention. It is to be understood that this general description applies to these components of the specific absorbent articles shown in FIG. 1 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). In addition to the absorbent composites of the present invention, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones and/or have a profile so as to be thicker in the center; hydrophilic gradients; gradients of the absorbent composite of the present invention, superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults.

The absorbent core can include other absorbent components that are often used in absorbent articles, for example, a dusting layer, a wicking or acquisition layer, or a secondary topsheet for increasing the wearer's comfort.

The topsheet is preferably compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), including apertured nonwovens; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, spunlace, carded, wet-laid, melt-blown, hydroentangled, hydroformed, hydroapertured, combinations of the above, or the like. The topsheet preferably comprises skin care composition(s) as described herein.

Typically, the backsheet is impervious to liquids (e.g., menses and/or urine), although a liquid pervious backsheet in combination with a liquid impervious liner or inner layer may also be useful herein. The backsheet preferably comprises a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished to provide a more clothlike appearance. The size of the backsheet is dictated by the size of the absorbent core and the exact absorbent article design selected. Furthermore, the backsheet may permit vapors to escape from the absorbent article (i.e., the backsheet is breathable) while still prevent exudates from passing through the backsheet. "Breathability" is believed to facilitate the decrease in relative humidity in the area between the skin and the absorbent article.

The backsheet and the topsheet are positioned adjacent the garment facing surface and the body facing surface, respectively, of the absorbent core. The absorbent core is preferably joined with the topsheet, the backsheet, or both in any manner as is known by attachment means (not shown in FIG. 1) such as those well known in the art. However, embodiments of the present invention are envisioned wherein portions or the entire absorbent core are unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

A preferred disposable absorbent article in which the wearer contacting surface is treated with skin care composition(s) are diapers. As used herein, the term "diaper" refers to an absorbent article generally worn by infants, and incontinent persons, that is worn about the lower torso of the wearer. In other words, the term "diaper" includes infant diapers, training pants, adult incontinence devices, etc.

FIG. 1 is a plan view of the diaper 50 useful in the methods of the present invention in its flat-out, uncontracted state (i.e., with elastic induced contraction pulled out) with portions of the structure being cut-away to more clearly show the construction of the diaper 50 and with the portion of the diaper 50 which faces away from the wearer (the outer surface) oriented towards the viewer. As shown in FIG. 1, the diaper 50 preferably comprises a liquid pervious topsheet 520; a liquid impervious backsheet 530 joined with the topsheet 520; an absorbent core 540 positioned between the topsheet 520 and the backsheet 530, the absorbent core 540 having a garment facing surface 542, a body facing surface 544, side edges 546, waist edges 548, and ears 549. The diaper 50 preferably further comprises elasticized leg cuffs 550; an elastic waist feature multiply designated as 560; and a fastening system generally multiply designated as 570.

The diaper 50 is shown in FIG. 1 to have an outer surface 52, an inner surface 54 corresponding to the body facing surface which is opposed to the outer surface 52, a first waist region 56, a second waist region 58, and a periphery 51 which is defined by the outer edges of the diaper 50 in which the longitudinal edges are designated 55 and the end edges are designated 57. (While the skilled artisan will recognize that a diaper is usually described in terms of having a pair of waist regions and a crotch region between the waist regions, in this application, for simplicity of terminology, the diaper 50 is described as having only waist regions including a portion of the diaper which would typically be designated as part of the crotch region). The body facing surface 54 of the diaper 50 comprises that portion of the diaper 50 which is positioned adjacent to the wearer's body during use. The body facing surface 54 generally is formed by at least a portion of the topsheet 520 and other components that may be joined to the topsheet 520, such as leg cuffs 550, as well as any regions to which the topsheet may not extend but which still contact the wearer, such as the waist feature 560, side panels and the like. The outer surface 52 comprises that portion of the diaper 50 which is positioned away from the wearer's body (i.e., the outer surface 52 generally is formed by at least a portion of the backsheet 530 and other components that may be joined to the backsheet 530). The first waist region 56 and the second waist region 58 extend, respectively, from the end edges 57 of the periphery 51 to the lateral centerline 53 of the diaper 50. FIG. 1 also shows the longitudinal centerline 59.

FIG. 1 shows a preferred embodiment of the diaper 50 in which the topsheet 520 and the backsheet 530 have length and width dimensions generally larger than those of the absorbent core 540. The elasticized leg cuffs 550 and the backsheet 530 extend beyond the edges of the absorbent core 540 to thereby form the periphery 51 of the diaper 50.

Diapers of the present invention can have a number of well known configurations, with the absorbent cores thereof being adapted to the present invention. Exemplary configurations are described generally in U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993. Each of these patents is incorporated herein by reference. Another diaper configuration to which the present invention can be readily adapted are described in co-pending U.S. patent application Ser. Nos. 08/203,456; filed on Feb. 28, 1994 and incorporated herein by reference. The absorbent cores of diapers described in these patents can be adapted in light of the teachings herein to include the absorbent composite of the present invention as an absorbent gelling material described therein.

A topsheet 520 which is particularly suitable for use in the diaper 50, is carded and thermally bonded by means well known to those skilled in the fabrics art. A satisfactory topsheet for the present invention comprises staple length polypropylene fibers having a denier of about 2.2 As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8.

The topsheet 520 of diaper 50 is preferably made of a hydrophilic material to promote rapid transfer of liquids (e.g., urine) through the topsheet. If the topsheet is made of a hydrophobic material, at least portions of the upper surface of the topsheet are treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. Nos. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

Alternatively, the topsheet may be in the form of an apertured formed film, which is preferred in feminine hygiene absorbent articles. Apertured formed films are useful because they are pervious to body liquids and yet non-absorbent and have a reduced tendency to allow liquids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Particularly preferred microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for use in feminine hygiene products is the formed film described in one or more of the above patents and marketed on sanitary napkins by The Procter & Gamble Company of Cincinnati, Ohio as "DRI-WEAVE®."

The body facing surface of the formed film topsheet can be hydrophilic so as to help body liquids to transfer through the topsheet faster than if the body surface was not hydrophilic so as to diminish the likelihood that liquid will flow off the topsheet rather than flowing into and being absorbed by the absorbent structure. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body facing surface of the topsheet can be made hydrophilic by treating it with a surfactant such as is described in the above referenced U.S. Pat. No. 4,950,254, incorporated herein by reference.

In a preferred embodiment of a diaper as described herein, the backsheet 530 has a modified hourglass shape extending beyond the absorbent core a minimum distance of about 1.3 cm to about 6.4 cm (about 0.5 to about 2.5 inch) around the entire diaper periphery.

The absorbent core 540 may take on any size or shape that is compatible with the diaper 50. One preferred embodiment of the diaper 50 has an asymmetric, modified T-shaped absorbent core 540 having ears in the first waist region but a generally rectangular shape in the second waist region. Exemplary absorbent materials for use as the absorbent core of articles useful in the present methods are described, e.g., in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

In a preferred embodiment, the diaper 50 further comprises elasticized leg cuffs 550 for providing improved containment of liquids and other body exudates; an elastic waist feature 560 that provides improved fit and containment; and a fastening system 570 which forms a side closure which maintains the first waist region 56 and the second waist region 58 in an overlapping configuration such that lateral tensions are maintained around the circumference of the diaper to maintain the diaper on the wearer. The diaper 50 may also comprise elasticized waist bands (not shown) and/or elasticized side panels (also not shown) in the waist regions 56 and 58 to provide an elastically extensible feature that provides a more comfortable and contouring fit and more effective application of the diaper 50.

The elasticized leg cuffs 550 can be constructed in a number of different configurations, including those described in U.S. Pat. No. 3,860,003; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo on Jan. 3, 1989, each being incorporated herein by reference. Absorbent articles having elasticized cuffs that are treated with a composition that may be useful herein are disclosed in co-pending U.S. patent application Ser. No. 08/766,386, filed Dec. 3, 1996, and co-pending U.S. patent application Ser. No. 08/840,039, filed Apr. 24, 1997, both of which are incorporated by reference.

The elasticized waist feature preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference.

The elasticized side panels may be constructed in a number of configurations. Examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference.

Exemplary fastening systems 570 are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. B1 4,662,875, issued to Hirotsu et al. on May 5, 1987; and U.S. Pat. No. 5,151,092, issued to Buell et al. on Sep. 29, 1992; each of which is incorporated herein by reference.

The diaper 50 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The fastening system is then applied to effect a side closure.

Of course, it will be recognized that any absorbent article design may be utilized to incorporate the skin care composition(s) of the present invention so long as the article is capable of delivering the skin care composition(s) to the skin during use. The disclosure above is merely for illustrative purposes.

The methods of the present invention may also employ training pants to effect delivery of the desired skin care composition. The term "training pants", as used herein, refers to disposable garments having fixed sides and leg openings designed for infant or adults wearers. Training pants (also referred in the art as "pull on" products) are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993, U.S. Pat. No. 5,569,234, issued to Buell et al. on Oct. 29, 1996, U.S. Pat. No. 4,940,464, issued to Van Gompel et al. on Jul. 10, 1990 and U.S. Pat. No. 5,092,861, issued to Nomura et al. on Mar. 3, 1992, the disclosure of each of which is incorporated herein by reference.

Another disposable absorbent article for use in the present methods are incontinence articles. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. Pat. No. 5,304,161 issued to Noel, et al. on Apr. 19, 1994 The disclosure of each of these references is incorporated herein.

Another disposable absorbent article for use in the present methods are feminine hygiene articles, such as sanitary napkins. Suitable feminine hygiene articles are disclosed in U.S. Pat. No. 4,556,146, issued to Swanson et al. on Dec. 3, 1985, U.S. Pat. No. B1 4,589,876, issued to Van Tilberg on Apr. 27, 1993, U.S. Pat. No. 4,687,478, issued to Van Tilburg on Aug. 18, 1997, U.S. Pat. No. 4,950,264, issued to Osborn, III on Aug. 21, 1990, U.S. Pat. No. 5,009,653, issued to Osborn, III on Apr. 23, 1991, U.S. Pat. No. 5,267,992, issued to Van Tilburg on Dec. 7, 1993, U.S. Pat. No. 5,389,094, issued to Lavash et al. on Feb. 14, 1995, U.S. Pat. No. 5,413,568, issued to Roach et al. on May 9, 1995, U.S. Pat. No. 5,460,623, issued to Emenaker et al. on Oct. 24, 1995, U.S. Pat. No. 5,489,283, issued Van Tilburg on Feb. 6, 1996, U.S. Pat. No. 5,569,231, issued to Emenaker et al. on Oct. 29, 1996, and U.S. Pat. No. 5,620,430, issued to Bamber on Apr. 15, 1997, the disclosure of each of which is incorporated by reference herein.

IV. Treating Articles with Skin Care Compositions

In preparing the present composition, the order and manner of mixing the various components of the present invention is not particularly critical. It is not necessary to mix the components together at elevated temperatures. It is found that the components may be thoroughly mixed to form a substantially uniform composition at temperatures which range from about 40° C. to about 100° C. Agitation is generally required. And it is found that viscous heat generated from agitation may be sufficient to raise the temperature of the mixture or composition so that a substantially uniform dispersion of components therein can be achieved. Sometimes, external heat may be added. It is preferred that the rheological agent be added to the carrier with agitation such that the rheological agent is mixed uniformly and/or activated (i.e., form a rheological structure). Where predispersions are used, the particulate materials and the predispersant are pre-mixed in a separate step before being added to the composition. However, predispersion of zinc oxide or other skin care ingredients are not required. These ingredients can be mixed with the carrier directly under sufficient agitation.

In preparing absorbent articles of the present invention, the skin care composition is applied such that during wear, at least some portion of the composition will transfer from the treated article to the wearer's skin. That is, skin care composition is either applied directly to one or more wearer contacting surfaces, or is applied in alternate locations or means such that the skin care composition is readily available for transfer from one or more wearer contacting surfaces during use without intervention by the user/caregiver. (For example, materials positioned beneath the wearer contacting surface, encapsulated compositions, etc.) Of course, to effectuate delivery of composition to those body regions most susceptible to contact with feces, it will be preferred to include the composition on the portion of the topsheet and cuffs that will contact the wearer's buttocks, genitals, intertriginous and anal regions during wear. Additionally, the composition may be applied to other article regions for delivery to one or more of the wearer's hips, abdomen, back, waist, sides, thighs, etc. Nonlimiting examples of suitable methods include spraying, printing (e.g., flexographic printing), coating (e.g., contact slot coating, gravure coating), dipping, extrusion, or combinations of these application techniques, e.g. spraying the skin care composition on a rotating surface, such as a calender roll, then transfers the composition to the desired portion of the article. Alternatively, the skin care composition may be applied to a substrate as a solid or semi-solid material via a variety of methods. It is to be understood that different application techniques/equipment are suited for materials with theological properties (e.g., apparent viscosity, elastic modulus) in a particularly range. For example, extrusion is suited for skin care composition having an apparent viscosity in the range from about 100,000 centipoise to about 1,000,000 centipoise, or an elastic modulus in the range from about 5,000 dyne/cm$^2$ to about 50,000 dyne/cm$^2$, at the processing temperature.

When applied to the article's topsheet, the manner of applying the composition to the article should preferably be such that the topsheet does not become saturated with the composition, at least in the region corresponding to the liquid discharge region of the article, if the composition is hydrophobic in nature. If the topsheet becomes saturated with the composition in the liquid discharge region, there is a greater potential for the composition to block the topsheet openings, reducing the ability of the topsheet to transmit liquid to the underlying absorbent core. Also, saturation of the topsheet is not required to obtain the skin care benefits. Similarly, saturation of other treated article components may not be necessary or desired to transfer sufficient composition for desired skin benefits. Particularly suitable application methods will apply the composition primarily to the outer surface of the topsheet of the article.

The minimum level of the composition to be applied to the article's wearer-contacting surface is an amount effective for providing the appearance, protective and/or skin conditioning benefits when the composition is delivered pursuant to the present invention. The level of composition applied will depend on various factors, including the article component treated, the relative amount of surface area of the wearer-contacting surface not treated with the composition, the composition's content and the like. In general, the composition is applied to the article in an amount ranging from about 0.05 mg/in$^2$ (0.0078 mg/cm$^2$) to about 100 mg/in$^2$ (15.6 mg/cm$^2$), preferably from about 0.1 mg/in$^2$ (0.016 mg/cm$^2$) to about 50 mg/in$^2$ (7.8 mg/cm$^2$), more prefeably from about 1 mg/in$^2$ (0.156 mg/cm$^2$) to about 25 mg/in$^2$ (3.9 mg/cm$^2$). It is recognized that the skin care compositions are relatively hydrophobic and to be applied to the topsheet of the article without covering the entire topsheet surface. It will be recognized that higher levels of skin care composition may be applied to other article components where fluid handling properties are not impacted (e.g., cuffs, waist band, side panels, etc.). It will also be recognized that for compositions that are relatively hydrophilic, higher add-on levels or complete coverage may be used on the topsheet without adversely impacting liquid handling properties to an unacceptable degree. Conversely, higher levels of a hydrophilic composition may be undesired when applied to components (e.g., cuff, waist) other than the topsheet, to avoid wicking of exudates to the edges of the article which may result in leakage.

Because the composition is preferably substantially immobilized on the surface of the region treated, relatively small amounts of composition are needed to deliver an effective amount of the skin care ingredient. It is believed that the ability to use low levels to impart the desired skin benefits is due to the fact that the composition is continuously, automatically delivered as articles are worn. As indicated, the ability to use relatively low levels of skin care composition, allows the article's topsheet to maintain its liquid transfer properties in the liquid discharge region.

The skin care composition may be applied nonuniformly to the wearer contacting surface of the article. By "nonuniform" it is meant that the amount, location, pattern of distribution, etc. of the composition can vary over the wearer-contacting surface, and may further vary over specific regions of the article. For example, to maintain the liquid handling performance of the topsheet, it may be desired to apply the composition nonuniformly to the topsheet, particularly if the composition is hydrophobic in nature. In this regard, some portions of the treated surface of the article (and regions thereof) can have greater or lesser amounts of composition, including portions of the surface that do not have any composition on it. When the composition is relatively hydrophobic, in one such preferred embodiment the surface of the topsheet will have regions where no composition is applied, particularly in areas of the topsheet that correspond to the crotch region of the article. As used herein, the crotch region of the article is the rectangle, defined below, that is centered longitudinally and laterally about the article's crotch point. The "crotch point" is determined by placing the article on a wearer in a standing position and then placing an extensible filament around the legs in a figure eight configuration. The point in the article corresponding to the point of intersection of the filament is deemed to be the crotch point of the article. (It is understood that the crotch point is determined by placing the absorbent article on a wearer in the intended manner and determining where the crossed filament would contact the article.) With regard to incontinence devices (e.g., diapers, adult incontinent articles), the length of the crotch region corresponds to 40% of the absorbent article's total length (i.e., in the y-dimension). With regard sanitary napkins, the length of the crotch region corresponds to 80% of the absorbent article's total length. The width of the crotch region is equivalent to the width of the widest absorbent core component as measured at the crotch point. (As used herein, "absorbent core" components are those materials involved with acquiring, transporting, distributing and/or storing body liquids. As such, the term absorbent core does not include the topsheet or backsheet of the absorbent article.) By way of illustration, for an incontinent article having a length of 20 in. and a core width at the crotch point of 4 in., the crotch region is the rectangle, centered on the crotch point, having a length of 8 in. and a width of 4 in.

Surprisingly, while the topsheet or other substrates are treated nonuniformly (e.g., microscopic or macroscopic regions where no composition is applied), during wear of the article, the composition is transferred to the wearer even in regions of the skin corresponding to untreated regions within the topsheet or other components. The amount and uniformity of composition transferred to the skin is believed to depend on several factors, including, for example, application pattern of the skin care composition, contact of the wearer's skin to the treated article surface, friction created during wear time between the wearer's skin and the treated region, warmth generated from wearer to enhance the transfer of the composition, the composition's properties, the materials which constitute the composition, and the like.

Where the composition is applied nonuniformly, any pattern may be utilized, including, for example, application of small droplets (obtained via, e.g., spraying) discrete dots (obtained via, e.g., gravure printing), stripes that run in the longitudinal or lateral direction of the article (obtained via contact slot coating), spirals that run in the longitudinal or lateral direction, etc., patterned prints, etc. In those embodiments where the topsheet comprises discrete, untreated regions, the percent open area of the region of the topsheet that corresponds to the crotch region of the article can vary widely. (As referred to herein, the "percent open area" of the topsheet is determined by (i) measuring the surface area of the topsheet that overlies the crotch region, (ii) measuring the total surface area of the untreated region(s) in this portion of the topsheet and (iii) dividing the measurement in (ii) by the measurement in (i). As used herein, "untreated" means a region of the topsheet having less than about 0.01 mg/in$^2$ (0.0016 mg/cm$^2$) of the composition. In this regard, the percent open area may be from about 1% to about 99%, from about 5% to about 95%, from about 10% to about 90%, from about 15% to about 85%, from about 20% to about 80%, from about 25% to about 75%, from about 30% to about 70%, or from about 35% to about 65%. The percent open area required to achieve the desired composition effect and the desired liquid handling properties of the topsheet will be dictated largely by the characteristics of the composition (in particular the composition's contents and its relative hydrophobicity/hydrophilicity properties). One skilled in the art will appreciate that the desired percent open area will be readily determined through routine experimentation.

In general, with compositions that are relatively hydrophobic and are to be applied such that regions of the topsheet are not coated with the composition, the composition is preferably applied to the article topsheet in an amount ranging from about 0.05 mg/in$^2$ (0.0078 mg/cm$^2$) to about 100 mg/in$^2$ (15.6 mg/cm$^2$), preferably from about 0.1 mg/in$^2$ (0.016 mg/cm$^2$) to about 50 mg/in$^2$ (7.8 mg/cm$^2$), more preferably from about 1 mg/in$^2$ (0.156 mg/cm$^2$) to about 25 mg/in$^2$ (3.9 mg/cm$^2$). It will be recognized that for compositions that are relatively hydrophilic, higher add-on levels may be used without adversely impacting liquid handling properties of the topsheet to an unacceptable degree. Of course, for articles having relatively high percent open areas in the crotch, greater add-on levels may be obtainable without adversely affecting liquid handling by the topsheet.

In one preferred embodiment of the present invention, the topsheet of the articles utilized will comprise stripes of the skin care composition that run in the article's longitudinal direction. These longitudinal stripes (or spirals) are separated by longitudinal stripes where little or no skin care composition is applied to the topsheet. In these embodiments, each stripe of composition will typically have a width of from about 0.1 in. to about 0.75 in., more typically from about 0.1 in. to about 0.5 in., and the width of the stripes containing no composition will typically be from about 0.1 in. to about 1 in., more typically from about 0.15 to about 0.5 in. These ranges are applicable to typical infant diaper designs. For larger products such as adult incontinent products, these ranges may be higher Skin care composition can also be applied in nonuniform patterns on other article components. In these cases, the open area is calculated by the rectangle defined by the perimeters of the skin care composition.

The composition can be applied to the article at any point during assembly. For example, the composition can be applied to the finished disposable absorbent product before it has been packaged. The composition can also be applied to a given component (e.g., topsheet, cuffs, sides, waist, etc.), at the converting site or by the material supplier, before it is combined with the other raw materials to form a finished disposable absorbent product. Again, the composition can be applied to other zones of the article such that the composition will migrate to one or more wearer contacting surfaces during use.

The composition is typically applied from a melt thereof to the article. In a preferred embodiment, the composition fully melts at a temperature significantly above room temperature, it is usually applied as a heated composition to the article. Typically, the composition is heated to a temperature in the range from about 35° C. to about 150° C., preferably from 40° C. to about 100° C., prior to being applied to the article. The skin care ingredient may be added to the composition prior to or after heating. Special care should be taken when heat-sensitive ingredients are used, for example, protease inhibitors or enzyme inhibitors. If added prior to heating, the temperature to which the composition is heated is selected so as not to denature the inhibitors. Alternatively, the inhibitors may be added to the pre-heated composition when it has cooled to a temperature that does not affect the inhibitors but is still sufficiently liquid to be applied to the article. Once the melted composition has been applied to the article, it is allowed to cool and solidify. Preferably, the application process is designed to aid in the cooling/set up of the composition.

In applying compositions to the articles, contact slot coating, spraying, gravure coating, extrusion coating methods are preferred. One such method involves slot coating of the composition on the article's topsheet, either before or after the topsheet is assembled with the other raw materials into a finished absorbent article.

Figure 2:
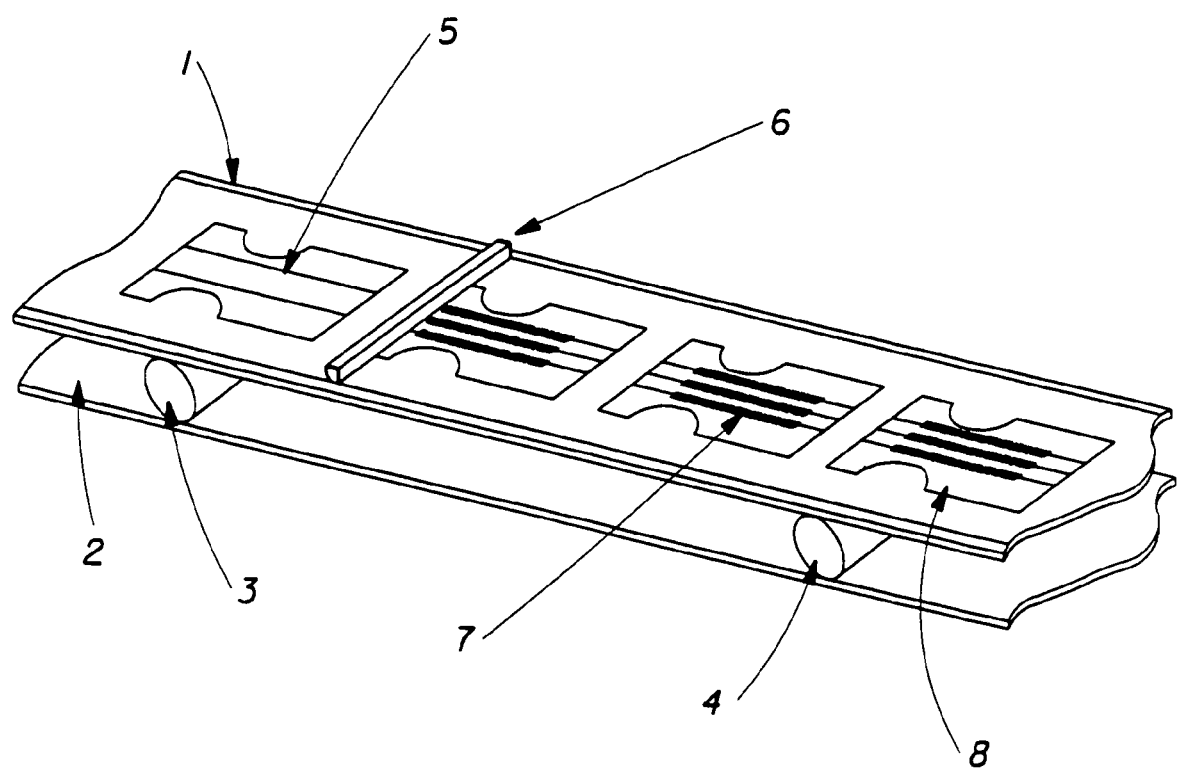
FIG. 2 is a schematic representation illustrating a preferred process for applying the lotion composition of the present invention to diaper topsheet and/or cuffs.

FIG. 2 illustrates a preferred method involving continuous or intermittent contact slot coating of the skin care composition onto a diaper topsheet and/or leg cuffs during the converting operation. Referring to FIG. 2, conveyor belt 1 advances in the direction shown by the arrows on turning rolls 3 and 4 and becomes returning conveyor belt 2. Conveyor belt 1 carries non-lotioned diaper 5 to contact slot coating station 6 where the topsheet and/or cuffs patch 7 is coated with a hot, molten (e.g., 170° F. or 77° C.) skin care composition. After leaving slot coating station 6, non-lotioned diaper 5 becomes lotioned diaper 8. The amount of lotion composition transferred to patch 7 is controlled by: (1) the rate at which the molten skin care composition is applied from contact slot coating station 6; and/or (2) the speed at which conveyor belt 1 travels under slot coating station 6.

Figure 3:
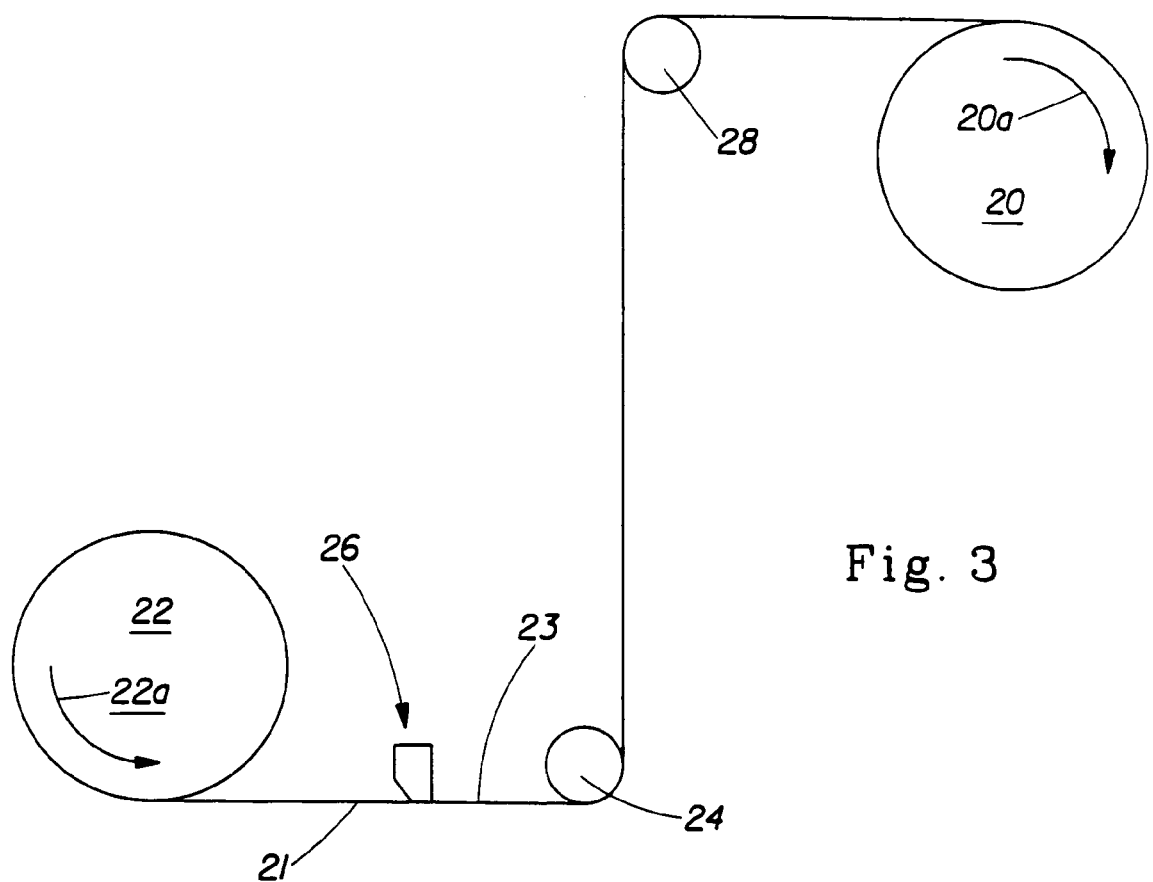
FIG. 3 is a schematic representation illustrating an alternative process for applying the lotion composition of the present invention to diaper topsheet and/or cuffs.

FIG. 3 illustrates an alternate preferred method involving contact slot coating of the skin care composition on the diaper topsheet and/or cuffs before the topsheet and/or cuffs are assembled with other raw materials into a finished product. Referring to FIG. 3, a nonwoven web 21 is unwound from parent roll 22 (rotating in the direction indicated by arrow 22a) and advanced to the contact slot coating station 26 where one side of the web is coated with a hot, molten (e.g., 170° F. or 77° C.) skin care composition. After leaving slot coating station 26, nonwoven web 21 becomes a lotioned web indicated by 23. Lotioned web 23 is then advanced around turning roll 24 and turning roll 28, and then wound up on lotioned parent roll 20 (rotating in the direction indicated by arrow 20a).

Test Methods a. Elastic Modulus Measurements

The theological properties (such as elastic modulus, viscosity) of the composition in the melt form are measured using a viscometer (available from TA Instruments of New Castle, Del. as model number CSL 100) in an oscillation mode. The measurements are conducted using a cone-and-plate measuring system, having a diameter of 40 mm and a gap of 60 micron. The measurement commences after about 100 seconds waiting time. And the measurements are conducted at two temperatures: 77° C. and 40° C. The elastic modulus measured at 10 rad/sec frequency and 0.2% strain is used to characterize the compositions. That is, all the elastic moduli disclosed and/or claimed herein are measured at the operating conditions given above.

b. Apparent Viscosity Measurements

The apparent viscosity is measured 77° C. and 40° C. using a rotational viscometer (available from Brookfield Engineering Laboratories, Inc. of Middleboro, Mass. as Model DV-3). The viscometer is operated at a shear rate of 10 rpm using a number 2 spindle.

c. Zero Shear Viscosity Measurements

Generally, the value for "zero shear viscosity" can be obtained by extrapolating a viscosity versus shear rate plot to a shear rate of zero. However, for plastic or pseudoplastic fluids which exhibit a yield behavior at low shear rate, the extrapolation method often does not fully and accurately describe the material. Alternatively, the "zero shear viscosity" can be approximated by a viscosity measured at very low shear rates. As used herein, the term "zero shear viscosity" is the value measured by a cone and plate viscometer (available from TA Instruments of New Castle, Del. as model number CSL 100), at very low shear rates (e.g., 1.0 sec$^{-1}$ or lower) and at a temperature of about 20° C.

d. Particle Size Measurements

A Focus Beam Reflectance Measurement (FBRM) Model M500 (available from Lasertec, Redman, Wash.) is used. The instrument is set up and operated according to manufacturer's instructions. The FBRM can be used to characterize solutions and/or suspensions. The FBRM can measure the number of particles and the mean particle chord length of the sample and determines the average particle size and distribution of the particulate materials in a liquid system.

VI. EXAMPLES

The following examples are illustrative of embodiments within the scope of the present invention. It should be understood that the present invention is not limited to the specific examples set forth below, as many variations thereof are possible without departing form the spirit and scope of the invention. All amounts of the various ingredients are expressed by weight percentages unless otherwise specified.

Each of the skin care composition examples described below is deposited on the topsheet of an absorbent article via a contact slot coater as disclosed herein. For example, a hot melt adhesive applicator head having multiple slots (Meltex EP11, available from Nordson Corp., Atlanta, Ga.) is suitable for use in the present invention. The composition is placed into a heated tank operating at a temperature of about 77° C. (i.e., about 170° F.). The composition is subsequently applied with a contact applicator onto the topsheet and cuffs of an article in a striped pattern where the stripes run in the article's longitudinal direction. Specifically, 5 stripes are applied, each stripe measuring about 0.25 inch in width (i.e., the substrate's lateral direction), about 11.7 inches in the longitudinal direction of the substrate, and at an add-on level of about 15.5 mg/in$^2$ (2.4 mg/cm$^2$). The distance between the stripes is about 0.31 inch

Example 1

A. Preparation of Skin Care Composition

An exemplary skin care composition of the present invention has the composition shown in TABLE 1 below:

TABLE 1

| Component | Weight % |
| --- | --- |
| Petrolatum[1] | 55.0 |
| Stearyl Alcohol[2] | 34.3 |
| ZnO Predispersion[3] | 6.7 |
| Fumed Silica[4] | 4.0 |

[1]PERFECTA ® available from Witco Corp., Greenwich, CT;
[2]CO1897 available from Procter and Gamble Co., Cincinnati, OH;
[3]75 wt % ZnO dispersed in 22 wt % % dispersant fluid and 3 wt % polyglyceryl ester wetting agent, available from Kobo Products, Inc., S. Plainfield, NJ; and
[4]CAB-O-SIL ® TS-720 available from Cabot Corporation, Tuscola, IL.

The composition is prepared by first mixing the petrolatum with stearyl alcohol in the melt. The rheological agent, i.e., fumed silica, is added to the melt mixture under a propeller agitation until substantially uniform and wetted. Zinc oxide predispersion is added to the melt mixture under high shear agitation until the mixture is substantially uniform, for example, at a temperature of about 77° C. (i.e., about 170° F.) for 30 minutes. High shear mixers such as a rotor-stator, homogenizer, a Gaulin® mill or colloid mill are suitable for the present invention. Alternatively, stearyl alcohol can be added to the melt mixture after all the other ingredients are mixed. In another alternative, fumed silica can be added last, i.e., after all other ingredients are mixed, if sufficient agitation is used to keep the particulate ingredients suspended till fumed silica is added and activated. The resulting composition has rheological properties suitable for use as a composition for topsheet application of an absorbent article. Specifically, the resulting composition is a solid or semi-solid at room temperature and has an apparent viscosity of about 100 centipoise and an elastic modulus of about 400 dynes/cm at about 77° C. and 0.1 rad/sec.

B. Preparation of a Treated Article by Contact Slot Coating

The composition is applied to a surface of an absorbent article using a contact slot coater according to the procedure disclosed above. The resultant absorbent article has a substantially uniform skin care composition disposed on at least a portion thereof.

Example 2

An exemplary skin care composition of the present invention has the composition shown in TABLE 2 below:

TABLE 2

| Component | Weight % |
| --- | --- |
| Petrolatum[1] | 42.0 |
| Stearyl Alcohol[2] | 26.3 |
| ZnO Predispersion[3] | 26.7 |
| Fumed Silica[4] | 5.0 |

[1]PERFECTA ® available from Witco Corp., Greenwich, CT;
[2]CO1897 available from Procter and Gamble Co., Cincinnati, OH;
[3]75 wt % ZnO dispersed in 22 wt % % dispersant fluid and 3 wt % polyglyceryl ester wetting agent, available from Kobo Products, Inc., S. Plainfield, NJ; and
[4]CAB-O-SIL ® TS-720 available from Cabot Corporation, Tuscola, IL.

The composition and the treated article are prepared in the same manner as Example 1. The resulting composition has rheological properties suitable for use as a composition for topsheet application of an absorbent article. Specifically, the resulting composition is a solid or semi-solid at room temperature and has an apparent viscosity of about 200 centipoise and an elastic modulus of about 2000 dynes/cm at about 77° C. and 0.1 rad/sec.

Example 3

An exemplary skin care composition of the present invention has the composition shown in TABLE 3 below:

TABLE 3

| Component | Weight % |
|---|---|
| Petrolatum[1] | 53.7 |
| Behenyl Alcohol[2] | 35.6 |
| ZnO Predispersion[3] | 6.7 |
| Organoclay[4] | 4.0 |

[1]PERFECTA ® available from Witco Corp., Greenwich, CT;
[2]LANETTE 22 available from Henkel Chemicals, Ambler, PA;
[3]75 wt % ZnO dispersed in 22 wt % % dispersant fluid and 3 wt % polyglyceryl ester wetting agent, available from Kobo Products, Inc., S. Plainfield, NJ; and
[4]Bentone 38 available from Rheox, Inc., Hightstown, NJ.

The composition and the treated article are prepared in the same manner as Example 1, except that behenyl alcohol and organoclay are used. The resulting composition has rheological properties suitable for use as a composition for topsheet application of an absorbent article. Specifically, the resulting composition is a solid or semi-solid at room temperature and has an apparent viscosity of about 8 centipoise and an elastic modulus of about 20 dynes/cm at about 77° C. and 0.1 rad/sec.

Example 4

An exemplary skin care composition of the present invention has the composition shown in TABLE 4 below:

TABLE 4

| Component | Weight % |
|---|---|
| Petrolatum[1] | 62.5 |
| Behenyl Alcohol[2] | 26.8 |
| ZnO Predispersion[3] | 6.7 |
| Organoclay[4] | 4.0 |

[1]PERFECTA ® available from Witco Corp., Greenwich, CT;
[2]LANETTE 22 available from Henkel Chemicals, Ambler, PA;
[3]75 wt % ZnO dispersed in 22 wt % % dispersant fluid and 3 wt % polyglyceryl ester wetting agent, available from Kobo Products, Inc., S. Plainfield, NJ; and
[4]BENTONE 38 available from Rheox, Inc., Hightstown, NJ.

The composition and the treated article are prepared in the same manner as Example 3. The resulting composition has rheological properties suitable for use as a composition for topsheet application of an absorbent article. Specifically, the resulting composition is a solid or semi-solid at room temperature and has an apparent viscosity of about 8 centipoise and an elastic modulus of about 20 dynes/cm at 77° C. and 0.1 rad/sec.

Example 5

An exemplary skin care composition of the present invention has the composition shown in TABLE 5 below:

TABLE 5

| Component | Weight % |
|---|---|
| Petrolatum[1] | 48.8 |
| Behenyl Alcohol[2] | 20.9 |
| ZnO Predispersion[3] | 26.8 |
| Organoclay[4] | 3.5 |

[1]PERFECTA ® available from Witco Corp., Greenwich, CT;
[2]LANETTE 22 available from Henkel Chemicals, Ambler, PA;
[3]75 wt % ZnO dispersed in 22 wt % % dispersant fluid and 3 wt % polyglyceryl ester wetting agent, available from Kobo Products, Inc., S. Plainfield, NJ; and
[4]BENTONE 38 available from Rheox, Inc., Hightstown, NJ.

The composition and the treated article are prepared in the same manner as Example 3. The resulting composition has rheological properties suitable for use as a composition for topsheet application of an absorbent article. Specifically, the resulting composition is a solid or semi-solid at room temperature and has an apparent viscosity of about 8 centipoise and an elastic modulus of about 20 dynes/cm at about 77° C. (i.e., about 170° F.) and 0.1 rad/sec.

Example 6

An exemplary skin care composition of the present invention has the composition shown in TABLE 6 below:

TABLE 6

| Component | Weight % |
|---|---|
| Petrolatum[1] | 53.0 |
| Stearyl Alcohol[2] | 33.1 |
| ZnO Predispersion[3] | 10.1 |
| Fumed Silica[4] | 3.9 |

[1]PERFECTA ® available from Witco Corp., Greenwich, CT;
[2]CO1897 available from Procter and Gamble Co., Cincinnati, OH;
[3]75 wt % ZnO dispersed in 22 wt % % dispersant fluid and 3 wt % polyglyceryl ester wetting agent, available from Kobo Products, Inc., S. Plainfield, NJ; and
[4]CAB-O-SIL ® TS-720 available from Cabot Corporation, Tuscola, IL.

The composition and the treated article are prepared in the same manner as Example 1. The resulting composition has a solid or semi-solid consistency at room temperature.

Example 7

Comparison with Commercial Creams or Ointments

This example compares the properties of the compositions of Examples 1–5 described hereinabove with commercially available creams or ointments. All compositions contain zinc oxide skin care ingredient.

TABLE 7

| Lotion | Temperature [C.] | Elastic Modulus [dynes/cm^2] | Viscosity (@0.1 rad/ces) [cps] | Viscosity (@100 rad/sec) [cps] | Yield Stress [dynes/cm^2] | Melt Point [C.] |
|---|---|---|---|---|---|---|
| Desitin | 77 | 8,000 | 700 | 4 | 200 | 35 |
| Ointment[a] | 40 | 8,000 | 700 | 10 | 20 | |
| Desitin | 77 | 400 | 600 | 2 | 70 | 45 |
| Creamy[a] | 40 | 6,000 | 3,000 | 10 | 60 | |
| J&J | 77 | 3,000 | 7,000 | 20 | 1,200 | 15 |
| Ointment[b] | 40 | 3,000 | 10,000 | 40 | 1,700 | |
| Balmex | 77 | 70 | 100 | 0.9 | 20 | 25 |
| Ointment[c] | 40 | 30,000 | 4,000 | 10 | 800 | |
| Diaper Guard[d] | 77 | 400 | 80 | 1 | 30 | 40 |
| | 40 | 20,000 | 2,000 | 9 | 800 | |
| Equate | 77 | 2,000 | 200 | 2 | 150 | 45 |
| Creamy[e] | 40 | 30,000 | 3,000 | 40 | 1,500 | |
| Example 1 | 77 | 400 | 100 | 0.6 | 20 | 50 |
| | 40 | >5,000,000 | * | * | * | |
| Example 2 | 77 | 2,000 | 200 | 1 | 80 | 50 |
| | 40 | >5,000,000 | * | * | * | |
| Example 3 | 77 | 20 | 8 | 0.2 | 10 | 50 |
| | 40 | >5,000,000 | * | * | * | |
| Example 4 | 77 | 20 | 8 | 0.2 | 10 | 50 |
| | 40 | >5,000,000 | * | * | * | |
| Example 5 | 77 | 40 | 40 | 0.5 | 20 | 55 |
| | 40 | >5,000,000 | * | * | * | |

* The skin care compositions have a semi-solid or solid consistency at the measurement temperature.
[a]available from Pfizer Consumer Health Care Group, Inc., NY, NY;
[b]available from Johnson & Johnson Consumer Products, Inc., Skillman, NJ;
[c]available from Block Drug Co., Inc., Jersey City, NJ;
[d]available from Del Pharmaceuticals, Inc., Farmingdale, NY; and
[e]available from Benjamin Ansehl Co., St. Louis, MO.

TABLE 7 shows that the compositions of the present invention are substantially non-flowable at a temperature of at least about 50° C. Importantly, this characteristic enables the compositions of the present invention to be substantially immobilized or "locked" on the skin-contacting surface of an absorbent article.

Example 8

Compositions 8(a) and 8(b) containing no immobilizing agent are prepared according to the procedure stated above. Composition 8(a) has 89% petrolatum, 7% zinc oxide predispersion and 4% fumed silica. Composition 8(b) has 68% petrolatum, 27% zinc oxide predispersion and 5% fumed silica. The melting temperature of both compositions is at least about 45° C. No immobilizing agent (e.g., stearyl alcohol) is needed to provide a solid or semi-solid consistency at room temperature.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for applying a skin care composition to at least a portion of an absorbent article comprising the steps of:
    (a) forming a skin care composition comprising:
        (i) a carrier;
        (ii) at least one skin care ingredient; and
        (iii) an effective amount of at least one rheological agent; and
    (b) applying the skin care composition to at least a portion of an absorbent article;
    wherein the composition has an elastic modulus of at least about 5 dynes/cm$^2$ measured at a strain rate of 0.2%, an oscillation frequency of 10 rad/sec, and a temperature of 77° C.

2. The process of claim 1 wherein step (b) is selected from the group consisting of spraying, printing, contact slot coating, gravure coating, dipping, extrusion, or combinations thereof.

3. The process of claim 2 wherein the process further comprises after step (b) cooling the skin care composition to a temperature sufficiently low such that the composition solidifies.

4. The process of claim 1 wherein the skin care composition comprises:
    from about 5 to about 95 wt % of the carrier;
    from about 0.001 to about 70 wt % of the skin care ingredient; and
    from about 0.1 to about 25 wt % of the rheological agent.

5. The process of claim 4 wherein
the carrier is selected from the group consisting of petroleum-based emollients, fatty acid esters, polysiloxanes, sucrose eater fatty acids, alkyl ethoxylates, humectants, lanolin and derivatives, and mixtures thereof;
the skin care ingredient is selected from the group consisting of allantoin, aluminum hydroxide gel, calamine, cocoa butter, dimethicone, cod liver oil, glycerine, kaolin, petrolatum, lanolin, mineral oil, shark liver oil, white petrolatum, talc, topical starch, zinc acetate, zinc carbonate, zinc oxide, live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, enzyme inhibitors, protease inhibitors, chelating agents, anti-microbials, proton donating agents, aloe extract, and mixtures thereof; and
the rheological agent is selected from the group consisting of untreated fumed silicas, treated fumed silicas, organoclays, metal fatty ester soaps, calcium silicates, polymeric thickeners, natural thickeners, organic thickeners, anionic surfactants, amphoteric surfactants, and mixtures thereof.

6. The process of claim 5 wherein the skin care ingredient is substantially insoluble in the carrier and comprises particles having an average particle size of less than about 1000 microns.

7. The process of claim 6 wherein the skin care ingredient comprises particles having an average particle size of less than about 100 microns.

8. The process claim 7 wherein the skin care ingredient is zinc oxide.

9. The process of claim 7 wherein the skin care ingredient comprises particles having an average particle size of less than about 50 microns.

10. The process of claim 3 wherein the portion of the absorbent article comprises a skin-contacting surface selected from the group consisting of a topsheet, a backsheet, a leg cuff, a side panel, a waist region, a secondary layer, a liner, and combinations thereof.

* * * * *

UNITED STATES PATENT AND TRADEMARK OFFICE
CERTIFICATE OF CORRECTION

| | | |
|---|---|---|
| PATENT NO. | : 7,033,645 B2 | Page 1 of 3 |
| APPLICATION NO. | : 10/845926 | |
| DATED | : April 25, 2006 | |
| INVENTOR(S) | : Joseph A. Gatto et al. | |

It is certified that error appears in the above-identified patent and that said Letters Patent is hereby corrected as shown below:

Title Page

Second line of (74) Attorney, Agent, or Firm, delete "KEn Patel" and insert

--Ken Patel--.

Column 3

Line 10, delete "theological" and insert -- rheological --.

Line 63, delete "theological" and insert -- rheological --.

Column 5

Line 39, delete "theological" and insert -- rheological --.

Column 6

Line 37, delete "theological" and insert -- rheological --.

Line 39, delete "theological" and insert -- rheological --.

Column 7

Line 45, delete "theological" and insert -- rheological --.

Column 8

Line 24-25, delete "theological" and insert -- rheological --.

Line 56, delete "theological" and insert -- rheological --.

Line 66, delete "theological" and insert -- rheological --.

UNITED STATES PATENT AND TRADEMARK OFFICE
CERTIFICATE OF CORRECTION

| | |
|---|---|
| PATENT NO. | : 7,033,645 B2 |
| APPLICATION NO. | : 10/845926 |
| DATED | : April 25, 2006 |
| INVENTOR(S) | : Joseph A. Gatto et al. |

It is certified that error appears in the above-identified patent and that said Letters Patent is hereby corrected as shown below:

Column 13

Line 3, delete "theological" and insert -- rheological --.

Line 47-48, delete "theological" and insert -- rheological --.

Line 54, delete "theological" and insert -- rheological --.

Line 55, delete "theological" and insert -- rheological --.

Line 56, delete "theological" and insert -- rheological --.

Line 60, delete "theological" and insert -- rheological --.

Line 62, delete "theological" and insert -- rheological --.

Line 67, delete "theological" and insert -- rheological --.

Column 14

Line 16-17, delete "theological" and insert -- rheological --.

Column 16

Line 25, delete "camauba" and insert -- carnauba --.

Column 18

Line 16-17, insert a hyphen -- - -- between "α" and "phenylethyl".

Column 20

Line 15, delete " ethoxylate" and insert -- ethoxylates --.

UNITED STATES PATENT AND TRADEMARK OFFICE
CERTIFICATE OF CORRECTION

PATENT NO. : 7,033,645 B2
APPLICATION NO. : 10/845926
DATED : April 25, 2006
INVENTOR(S) : Joseph A. Gatto et al.

It is certified that error appears in the above-identified patent and that said Letters Patent is hereby corrected as shown below:

<u>Column 22</u>

Line 63, delete "camauba" and insert -- carnauba --.

<u>Column 33</u>

Line 44, delete "preferably" and insert -- preferably --.

<u>Column 36</u>

Line 62, delete "theological" and insert -- rheological --.

Signed and Sealed this

Thirteenth Day of November, 2007

JON W. DUDAS
*Director of the United States Patent and Trademark Office*